(12) United States Patent
Miyashita et al.

(10) Patent No.: US 10,903,433 B2
(45) Date of Patent: Jan. 26, 2021

(54) ORGANIC COMPOUND, AND PHOTOELECTRIC CONVERSION ELEMENT AND IMAGING DEVICE USING THE ORGANIC COMPOUND

(71) Applicant: CANON KABUSHIKI KAISHA, Tokyo (JP)

(72) Inventors: Hirokazu Miyashita, Ebina (JP); Naoki Yamada, Inagi (JP); Hiroki Ohrui, Kawasaki (JP); Hironobu Iwawaki, Yokohama (JP); Yosuke Nishide, Kawasaki (JP); Jun Kamatani, Tokyo (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 133 days.

(21) Appl. No.: 16/157,655

(22) Filed: Oct. 11, 2018

(65) Prior Publication Data

US 2019/0115545 A1 Apr. 18, 2019

(30) Foreign Application Priority Data

Oct. 16, 2017 (JP) ................................. 2017-200399

(51) Int. Cl.
| | | |
|---|---|---|
| *C07D 409/04* | (2006.01) | |
| *H01L 51/00* | (2006.01) | |
| *H01L 51/42* | (2006.01) | |
| *C07D 221/18* | (2006.01) | |
| *H04N 5/232* | (2006.01) | |
| *H04N 5/225* | (2006.01) | |
| *H04N 5/374* | (2011.01) | |
| *H01L 27/30* | (2006.01) | |

(52) U.S. Cl.
CPC ........ *H01L 51/0072* (2013.01); *C07D 221/18* (2013.01); *C07D 409/04* (2013.01); *H01L 51/0051* (2013.01); *H01L 51/0052* (2013.01); *H01L 51/0068* (2013.01); *H01L 51/4273* (2013.01); *H04N 5/2252* (2013.01); *H04N 5/23203* (2013.01); *H04N 5/374* (2013.01); *H01L 27/307* (2013.01); *H01L 51/0046* (2013.01); *H01L 51/0053* (2013.01)

(58) Field of Classification Search
CPC ..... H01L 51/00; C07D 215/33; C07D 221/18; C07D 409/04; C07D 215/32
See application file for complete search history.

(56) References Cited

U.S. PATENT DOCUMENTS

| | | | | |
|---|---|---|---|---|
| 7,977,570 B2* | 7/2011 | Shigaki | ............... | C09B 23/0066 136/250 |
| 2011/0056562 A1* | 3/2011 | Hamano | ................ | C09B 23/04 136/263 |
| 2014/0374733 A1* | 12/2014 | Hirai | ................... | C07D 455/03 257/40 |

\* cited by examiner

*Primary Examiner* — D Margaret M Seaman
(74) *Attorney, Agent, or Firm* — Canon U.S.A., Inc. IP Division

(57) ABSTRACT

An organic compound represented by the following formula [1] has a high absorption coefficient in a long wavelength region and is thermally stable.

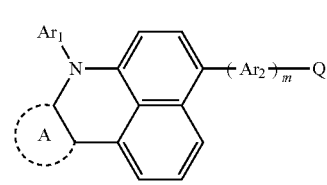

[1]

In formula [1], $Ar_1$ and $Ar_2$ each represent a group independently selected from the group consisting of aryl group and heterocyclic groups, and A represents a cyclic structure. m represents an integer of 0 to 2. Q represents a structure represented by one of the following formulas [1-1] and [1-2], wherein n represents an integer of 0 to 2, and when n is 2, the two $R_4$'s may be the same as or different from each other, and the two $R_5$'s may be the same as or different from each other.

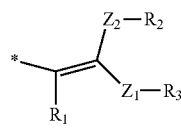

[1-1]

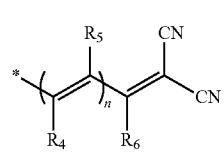

[1-2]

16 Claims, 4 Drawing Sheets

ORGANIC COMPOUND, AND PHOTOELECTRIC CONVERSION ELEMENT AND IMAGING DEVICE USING THE ORGANIC COMPOUND

BACKGROUND OF THE INVENTION

Field of the Invention

The present disclosure relates to an organic compound and to a photoelectric conversion element and an imaging device using the organic compound.

Description of the Related Art

Photoelectric conversion elements are operable to receive external light and convert the energy of the light into electrical energy. Solid-state imaging devices using this function of the photoelectric conversion element are widely used. The solid-state imaging device includes a light sensor in which a plurality of photoelectric conversion elements are two-dimensionally arranged.

Also, organic photoelectric conversion elements including a photoelectric conversion portion containing an organic compound have been being developed. The organic compound has a high absorption coefficient and flexibility, and the use of the organic compound in organic photoelectric conversion elements is expected to increase the sensitivity of the imaging device, to reduce the thickness and weight of the imaging device, and to enable the imaging device to be flexible.

In general, the optical absorption band of an organic compound depends greatly on the size of the molecule of the compound. There have been disclosed few compounds that have an optical absorption band in a long wavelength region in spite of having a low molecular weight. The wavelength region of light that is converted into electrical energy by an organic photoelectric conversion element depends on the absorption band of the organic compound used in the photoelectric conversion portion. Accordingly, an organic compound that can exhibit high absorption in a long wavelength region as well is desired for an organic photoelectric conversion element capable of photoelectric conversion over the entire region of visible wavelengths.

US 2011/0056562 (hereinafter referred to as PTL 1) discloses an organic photoelectric conversion element using the following compound (1-A):

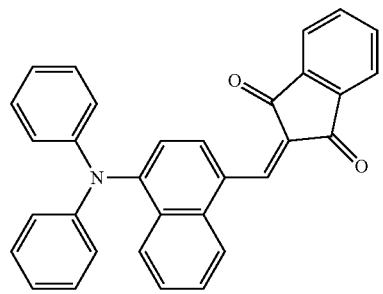

1-A

Compound (1-A) disclosed in PTL 1 has an absorption band having a maximum absorption in a wavelength range from a blue region (around a wavelength of 450 nm) to a green region (around a wavelength of 500 nm), exhibiting a low absorption in a red region (around a wavelength of 600 nm). Accordingly, the photoelectric conversion efficiency of organic photoelectric conversion elements using this compound is low particularly in a red region (around a wavelength of 600 nm).

In addition, compound (1-A) has a low glass transition temperature. Accordingly, the compound has a risk of being crystallized in a process with a large thermal load. This may degrade the properties of the organic photoelectric conversion element.

SUMMARY OF THE INVENTION

The present disclosure provides a thermally stable organic compound having an absorption band in a long wavelength region.

According to an aspect of the present disclosure, an organic compound represented by the following formula [1] is provided:

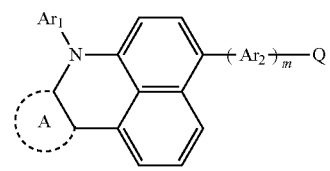

[1]

In formula [1], $Ar_1$ and $Ar_2$ each represent a group independently selected from the group consisting of aryl groups having a carbon number of 6 to 18 and heteroaryl groups having a carbon number of 3 to 15.

In formula [1], A represents a cyclic structure selected from the group consisting of a benzene ring, a naphthalene ring, a phenanthrene ring, a fluorene ring, a pyridine ring, a thiophene ring, a benzothiophene ring, a furan ring, and a benzofuran ring.

In formula [1], m represents an integer of 0 to 2, and when m is 2, the two $Ar_2$'s may be the same as or different from each other.

In formula [1], Q represents an electron-withdrawing substituent represented by one of the following formulas [1-1] and [1-2]:

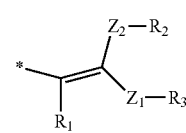

[1-1]

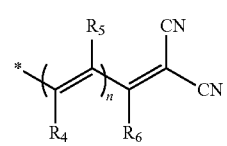

[1-2]

In formulas [1-1] and [1-2], * represents a bonding site, and $R_1$ to $R_6$ each represent a chemical species independently selected from the group consisting of a hydrogen atom, a cyano group, an amino group, alkylamino groups having a carbon number of 1 to 4, amide groups having a carbon number of 1 to 4, alkenyl groups having a carbon number of 2 to 4, alkynyl groups having a carbon number of 2 to 4, a methoxy group, an ethoxy group, a methyl group, an ethyl group, an isopropyl group, a tert-butyl group, a phenyl group, and a pyridyl group. $R_2$ and $R_3$ may be bound to each other to form a ring, and $R_4$ and $R_6$ may be bound to each other to form a ring.

In formula [1-1], $Z_1$ and $Z_2$ each represent a structure represented by one of the following formulas [2-1] to [2-3]:

[2-1]

[2-2]

[2-3]

In formula [1-2], * represents a bonding site, and n represents an integer of 0 to 2. When n is 2, the two $R_4$'s may be the same as or different from each other, and the two $R_5$'s may be the same as or different from each other.

Further features will become apparent from the following description of exemplary embodiments with reference to the attached drawings.

DESCRIPTION OF THE EMBODIMENTS

Organic Compound of the Present Disclosure

Figure 1:
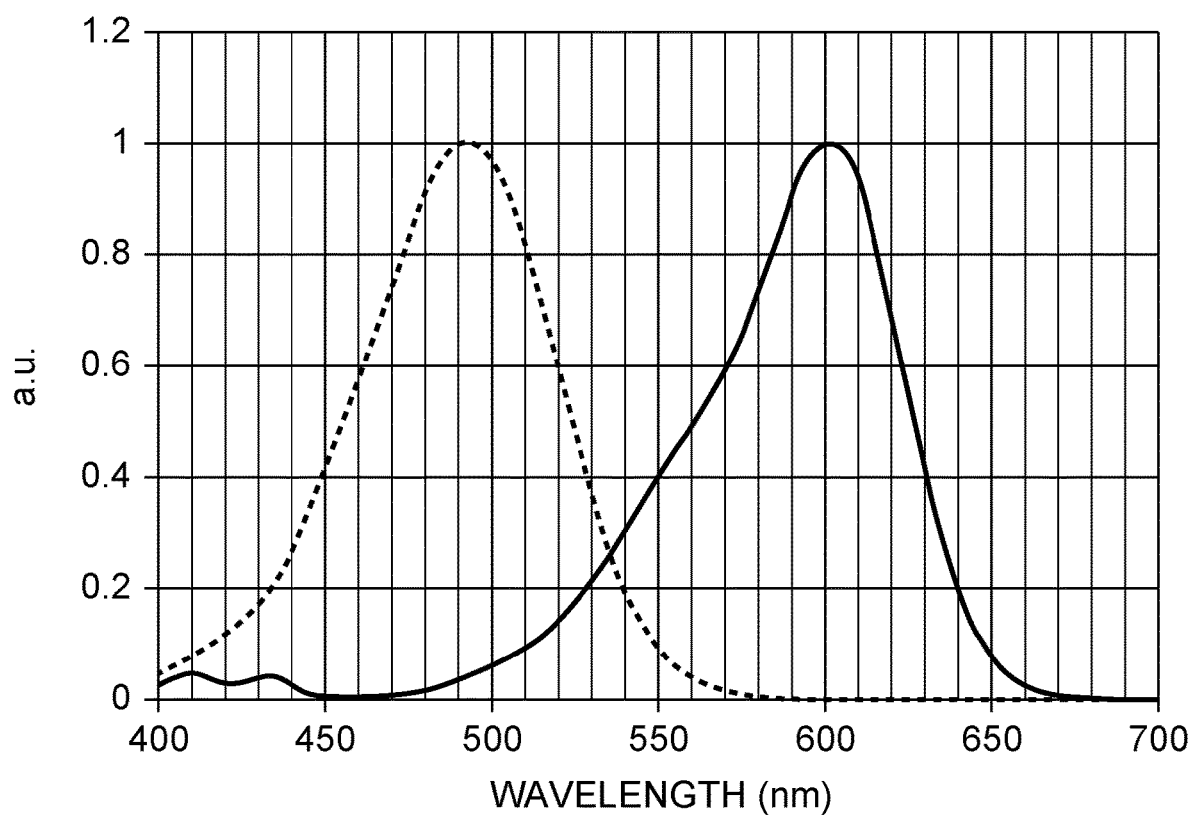
FIG. 1 is a plot of absorption spectra of Exemplified Compound A2 and Comparative Compound 1 each in a diluted chloroform solution.

The organic compound of the present disclosure will first be described. The organic compound of the present disclosure is represented by the following general formula [1]:

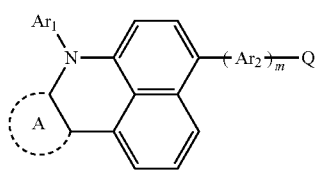

[1]

In general formula [1], $Ar_1$ and $Ar_2$ each represent a group independently selected from the group consisting of aryl groups having a carbon number of 6 to 18 and heteroaryl groups having a carbon number of 3 to 15.

Exemplary aryl groups having a carbon number of 6 to 18, represented by $Ar_1$ and $Ar_2$ include phenyl, biphenyl, terphenyl, naphthyl, phenanthrenyl, chrysenyl, pyrenyl, fluorenyl, fluoranthenyl, and triphenylenyl. In some embodiments, the aryl group may be phenyl, biphenyl, or naphthyl from the viewpoint of sublimation. These aryl groups are stable and have a low molecular weight.

Exemplary heteroaryl groups having a carbon number of 3 to 15, represented by $Ar_1$ or $Ar_2$ include pyridyl, pyrazyl, triazyl, pyrrole, furanyl, thienyl, thienothienyl, imidazole, pyrazole, oxazole, thiazole, benzothienyl, dibenzothienyl, benzofuranyl, and dibenzofuranyl. In some embodiments, the heteroaryl group may be pyridyl, thienyl, thienothienyl, benzothienyl, furanyl, or benzofuranyl from the viewpoint of sublimation. These heteroaryl are chemically stable and have a low molecular weight.

In an embodiment, it may be beneficial that $Ar_2$ be thienyl, thienothienyl, or furanyl.

$Ar_1$ and $Ar_2$ may have a substituent selected from the group consisting of halogen atoms, a cyano group, alkyl groups having a carbon number of 1 to 6, alkoxy groups having a carbon number of 1 to 6, a trifluoromethyl group, a phenyl group, a tolyl group, a xylyl group, and a mesityl group.

Examples of the halogen atom that may be substituted for hydrogen of $Ar_1$ or $Ar_2$ include chlorine, bromine, iodine, and fluorine. In some embodiments, fluorine may be beneficial.

Examples of the alkyl group having a carbon number of 1 to 6 that may be substituted for hydrogen of $Ar_1$ or $Ar_2$ include methyl, ethyl, n-propyl, isopropyl, n-butyl, tert-butyl, sec-butyl, and cyclohexyl. In some embodiments, methyl or tert-butyl may be beneficial.

Examples of the alkoxy group having a carbon number of 1 to 6 that may be substituted for hydrogen of $Ar_1$ or $Ar_2$ include methoxy, ethoxy, n-propoxy, isopropoxy, n-butoxy, tert-butoxy, and sec-butoxy. In some embodiments, methoxy or ethoxy may be beneficial.

In general formula [1], A represents a cyclic structure selected from the group consisting of a benzene ring, a naphthalene ring, a phenanthrene ring, a fluorene ring, a pyridine ring, a thiophene ring, a benzothiophene ring, a furan ring, and a benzofuran ring and is bound to the compound with a covalent bond. In some embodiments, A may be a benzene ring, a naphthalene ring, a phenanthrene ring, or a fluorene ring. These cyclic structures are chemically stable. In an embodiment, A may be a benzene or naphthalene ring, which has a low molecular weight, from the viewpoint of sublimation.

Cyclic structure A may have a substituent selected from among the substituents cited as the substituent of $Ar_1$ and $Ar_2$.

In general formula [1], m represents an integer of 0 to 2, and when m is 2, the two $Ar_2$'s may be the same as or different from each other.

In general formula [1], Q represents an electron-withdrawing substituent represented by one of the following general formulas [1-1] and [1-2]:

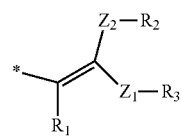

[1-1]

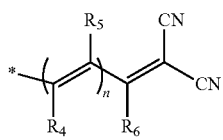

[1-2]

In general formulas [1-1] and [1-2], * represents a bonding site, and $R_1$ to $R_6$ each represent a chemical species independently selected from the group consisting of a hydrogen atom, a cyano group, an amino group, alkylamino groups having a carbon number of 1 to 4, amide groups having a carbon number of 1 to 4, alkenyl groups having a carbon number of 2 to 4, alkynyl groups having a carbon number of 2 to 4, a methoxy group, an ethoxy group, a methyl group, an ethyl group, an isopropyl group, a tert-butyl group, a phenyl group, and a pyridyl group.

Exemplary alkylamino groups having a carbon number of 1 to 4, represented by $R_1$ to $R_6$ include N-methylamino, N-ethylamino, N,N-dimethylamino, and N,N-diethylamino.

Exemplary amide groups having a carbon number of 1 to 4, represented by $R_1$ to $R_6$ include methylamide, ethylamide, isopropylamide, and n-butylamide.

Exemplary alkenyl groups having a carbon number of 2 to 4, represented by $R_1$ to $R_6$ include vinyl, propenyl, and 1-butenyl.

Exemplary alkynyl groups having a carbon number of 2 to 4, represented by $R_1$ to $R_6$ include ethynyl, n-1-propynyl, and n-2-butynyl.

The groups represented by $R_1$ to $R_6$ each may have a substituent selected from the group consisting of a chlorine atom, a fluorine atom, a cyano group, a methyl group, a tert-butyl group, a methoxy group, an ethoxy group, a phenyl group, a tolyl group, a xylyl group, and a mesityl group.

$R_2$ and $R_3$ may be bound to each other to form a ring, and $R_4$ and $R_6$ may be bound to each other to form a ring.

In general formula [1-1], $Z_1$ and $Z_2$ each represent a structure represented by one of the following general formulas [2-1] to [2-3]:

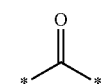
[2-1]

[2-2]

[2-3]

In general formula [1-2], * represents a bonding site, and n represents an integer of 0 to 2. When n is 2, the two $R_4$'s may be the same as or different from each other, and the two $R_5$'s may be the same as or different from each other.

In an embodiment, Q of the organic compound represented by general formula [1] may be represented by general formula [1-1], and $R_2$ and $R_3$ may be bound to each other to form a ring. The organic compound having such a structure has an absorption band in a longer wavelength region and is more thermally stable. For example, $R_2$ and $R_3$ may form a ring represented by any one of the following general formulas [3-1] to [3-9]:

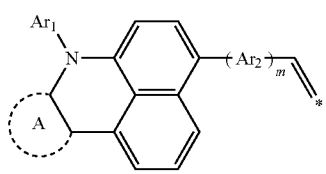

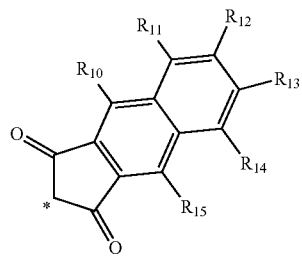
[3-1]

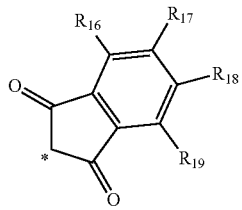
[3-2]

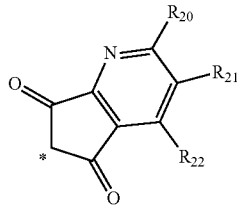
[3-3]

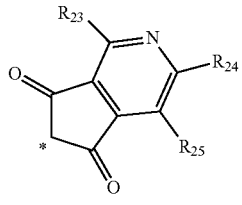
[3-4]

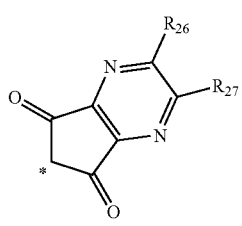
[3-5]

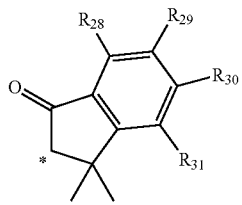
[3-6]

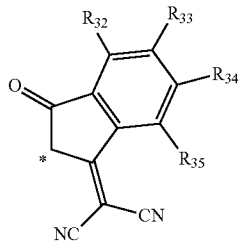
[3-7]

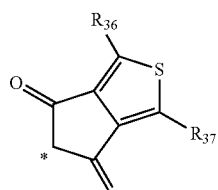
[3-8]

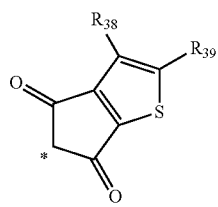
[3-9]

In general formulas [3-1] to [3-9], $R_{10}$ to $R_{39}$ each represent a chemical species independently selected from the group consisting of a hydrogen atom, a fluorine atom, a chlorine atom, a cyano group, a methyl group, a tert-butyl group, a methoxy group, an ethoxy group, a trifluoromethyl group, a phenyl group, a tolyl group, a xylyl group, and a mesityl group.

In an embodiment, $Z_1$ and $Z_2$ of the organic compound of general formula [1] may be represented by general formula [2-1]. The organic compound having such a structure is more thermally stable. More specifically, the organic compound may be represented by the following general formula [4]:

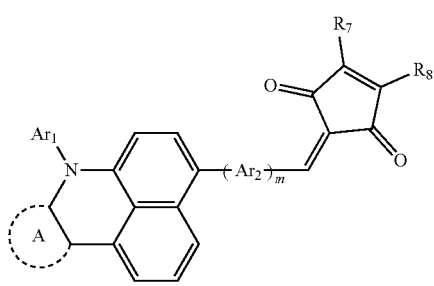
[4]

In general formula [4], $R_7$ and $R_8$ each represent a chemical species independently selected from the group consisting of a hydrogen atom, a fluorine atom, a chlorine atom, a cyano group, a methyl group, a tert-butyl group, a methoxy group, an ethoxy group, a trifluoromethyl group, a phenyl group, a tolyl group, a xylyl group, a pyridyl group, and a thienyl group.

Also, $R_7$ and $R_8$ may have a substituent selected from the group consisting of a fluorine atom, a cyano group, a methyl group, a tert-butyl group, a methoxy group, a phenyl group, and a thienyl group.

$R_7$ and $R_8$ may be bound to each other to form a ring. The ring formed by $R_7$ and $R_8$ may be one selected from the group consisting of a benzene ring, a naphthalene ring, a pyridine ring, a pyrimidine ring, a pyrazine ring, a pyridazine ring, a quinoline ring, an isoquinoline ring, a quinoxaline ring, a thiophene ring, a benzothiophene ring, a furan ring, and a benzofuran ring.

Beneficially, Q of the organic compound represented by general formula [1] is represented by general formula [1-2], and in which n is 0. The organic compound having such a structure has a low molecular weight and can be purified by sublimation at a low temperature. For example, in an embodiment, the organic compound may be represented by the following general formula [5]:

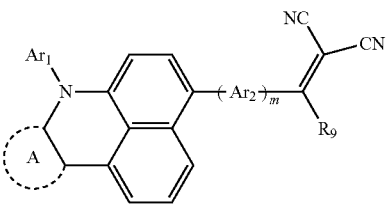
[5]

In general formula [5], $R_9$ represents a chemical species independently selected from the group consisting of a hydrogen atom, a fluorine atom, a chlorine atom, a cyano group, a methyl group, a tert-butyl group, a methoxy group, an ethoxy group, a trifluoromethyl group, a phenyl group, a tolyl group, a xylyl group, a pyridyl group, and a thienyl group.

Also, $R_9$ may have a substituent selected from the group consisting of a fluorine atom, a cyano group, a methyl group, a tert-butyl group, a methoxy group, and a phenyl group.

Characteristics of the Organic Compound

The characteristics of the organic compound of the present disclosure will be described.

The organic compound of the present disclosure has a chemical structure in which an electron-donating skeleton and an electron-withdrawing substituent represented by Q are bound to each other directly or with $Ar_2$ therebetween, as represented by general formula [1].

Accordingly, the organic compound of the present disclosure has the following characteristics (1) to (3):

(1) being absorbent of light in a long wavelength region;
(2) having a high absorption coefficient; and
(3) being thermally stable.

The characteristics (1) to (3) will be described below.

(1) Being Absorbent of Light in a Long Wavelength Region

In general, the photoelectric conversion layer of photoelectric conversion elements is an intermixed layer containing a p-type organic semiconductor and an n-type organic semiconductor so as to increase photoelectric conversion efficiency. p-Type organic semiconductors are electron-donating organic compounds, and n-type organic semiconductors are electron-withdrawing organic compounds.

In addition, the intermixed layer containing two compounds having different absorption bands is expected to enable photoelectric conversion over the entire region of visible wavelengths. For example, fullerene C60, which is widely used as an n-type organic semiconductor of photoelectric conversion elements, has an absorption band in a wavelength region of 380 nm to 500 nm, which corresponds to the region from blue (around 450 nm) to green (around 500 nm). In contrast, there are few reports of organic compounds having a strong absorption band in a long wavelength region (for example, a red region around 600 nm). This is because the absorption band of an organic compound depends greatly on the π-conjugation length of the molecule, that is, the molecular size. If a molecule having an absorption band in a long wavelength region is designed, the molecular weight increases, and the compound becomes difficult to sublime. Non-sublimable compounds are difficult to purify by sublimation. Consequently, the photoelectric conversion element is adversely affected by impurities, reducing performance and stability.

The organic compound of the present disclosure has a structure in which an electron-donating skeleton and an electron-withdrawing substituent are bound to each other. This organic compound therefore has an absorption band in a long wavelength region while having a low molecular weight and being highly sublimable.

FIG. 1 shows a comparison between absorption spectra of Exemplified Compound A2 according to an embodiment of the preset disclosure and Comparative Compound 1 each in a diluted chloroform solution. Comparative Compound 1 is Compound 1-A disclosed in PTL 1. The absorption spectra were each obtained by measuring a solution of the compound in diluted chloroform in a quartz cell with a spectrophotometer V-560 manufactured by JASCO Corporation.

The maximum absorption wavelength ($\lambda$max) of Comparative Compound 1 (dotted line) was 492 nm, while the maximum absorption wavelength ($\lambda$max) of Exemplified Compound A2 (solid line) according to an embodiment of the present disclosure was 600 nm.

These results suggest that the organic compound of the present disclosure has an absorption band in a long wavelength region. Accordingly, by providing a photoelectric conversion layer defined by an intermixed layer containing the organic compound according to an embodiment of the present disclosure as a p-type organic semiconductor (absorbing light in the red region) and an organic compound such as fullerene C60 (absorbing light in a region from blue to green) as an n-type organic semiconductor for a photoelectric conversion element, the photoelectric conversion element can convert light in the entire region of visible wavelengths into electrical energy.

(2) Having a High Absorption Coefficient

It is desired that the organic compounds in the photoelectric conversion layer of organic photoelectric conversion elements have a high absorption coefficient. This is because the use of an organic compound having a high absorption coefficient is expected to increase sensitivity. In addition, the use of such an organic compound enables the formation of a thin photoelectric conversion layer to which a high electric field can be applied at a reduced voltage; hence a higher photoelectric conversion efficiency is expected.

The electron-donating portion of the organic compound of the present disclosure has a planar skeleton. This structure restricts the structural change of the compound in an excited state, and the organic compound has a high coefficient of absorption resulting from charge-transfer (CT) transition between the electron-donating portion and the electron-withdrawing portion.

The molar absorption coefficients of Exemplified Compound A2 according to an embodiment of the preset disclosure and Comparative Compound 1 will now be compared. The absorption spectra were each determined by measuring a solution of the compound in chloroform in a quartz cell with a spectrophotometer V-560 manufactured by JASCO Corporation.

The molar absorption coefficient of Comparison Compound 1 at the maximum absorption wavelength ($\lambda$max) was $4.0 \times 10^4$ M$^{-1}$cm$^{-1}$, while the molar absorption coefficient of Exemplified Compound A2 at the maximum absorption wavelength ($\lambda$max) was $7.0 \times 10^4$ M$^{-1}$cm$^{-1}$.

In the molecular structure of Comparative Example 1, the hydrogen atom at the peri-positions of the naphthalene ring and the phenyl groups of the diphenylamine sterically repel each other, so that the electron-donating portion is twisted. On the other hand, Exemplified Compound A2 has a structure in which the CT transition moments of the electron-donating portion and the electron-withdrawing portion are likely to align with each other due to the planar skeleton. The present inventors assume that this is the reason why the organic compound of the present disclosure exhibits a strong absorption.

Thus, the use of the organic compound of the present disclosure in the photoelectric conversion layer provides a sensitive organic photoelectric conversion element.

(3) Being Thermally Stable

Organic photoelectric conversion elements are required to be thermally stable under the high-temperature condition of a process step for forming color filters and a process step for wire bonding for, for example, mounting photosensors.

The organic compound of the present disclosure has a planar skeleton and exhibits large intermolecular interaction caused by molecular packing. Consequently, the organic compound is kept amorphous even at high temperature; hence the organic compound has a high glass transition temperature.

Table 1 shows the measurement results of Exemplified Compound A2 and Comparative Example 1. The glass transition temperatures were each measured by differential scanning calorimetry (DSC). The DSC measurement for determining glass transition temperature was performed by rapidly cooling the sample from a temperature over the melting point to change the sample into an amorphous state and then heating the sample. For this measurement, Pyris 1 DSC manufactured by PerkinElmer was used.

The glass transition temperature of Comparative Example 1 was 70° C., while the glass transition temperature of Exemplified Compound A2 was 125° C.

Thus, the use of the organic compound of the present disclosure in the photoelectric conversion layer provides a thermally stable organic photoelectric conversion element.

Table 1 also shows the molecular structures, the maximum absorption wavelengths, the molar absorption coefficients, and the glass transition temperatures of each of Exemplified Compound A2 and Comparative Compound 1 together.

TABLE 1

|  | Structure | Maximum absorption wavelength ($\lambda$max) | Molar absorption coefficient @$\lambda$max | Glass transition temperature |
|---|---|---|---|---|
| Exemplified Compound A2 | 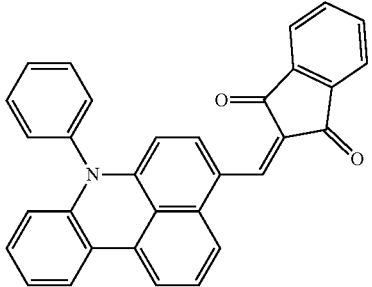 [SMILES: O=C1C(=Cc2ccc3c4c(cccc24)-c2ccccc2N3c2ccccc2)C(=O)c2ccccc21] | 600 nm | $7.0 \times 10^4$ M$^{-1}$ cm$^{-1}$ | 125° C. |

TABLE 1-continued

| | Structure | Maximum absorption wavelength (λmax) | Molar absorption coefficient @λmax | Glass transition temperature |
|---|---|---|---|---|
| Comparative Example 1 | 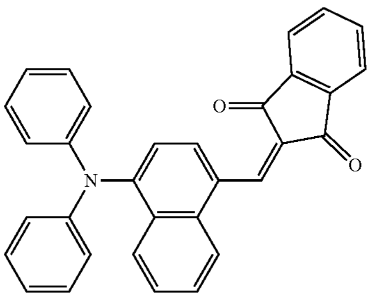 [SMILES: O=C1C(=Cc2ccc(N(c3ccccc3)c3ccccc3)c3ccccc23)C(=O)c2ccccc21] | 492 nm | $4.0 \times 10^4\ M^{-1}\ cm^{-1}$ | 70° C. |

Exemplified Organic Compound of the Present Disclosure

Structural formulas of some of the organic compounds according to the present disclosure are shown below. However, it should be appreciated that the organic compound of the present disclosure is not limited to the following exemplified compounds.

A1
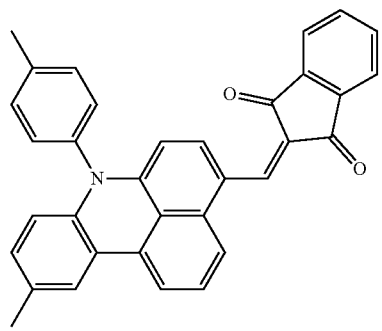

A2
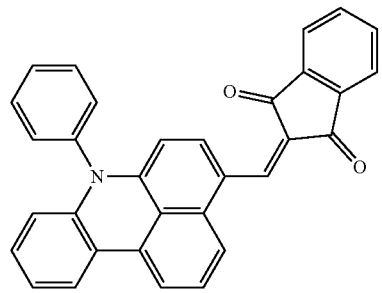

A3
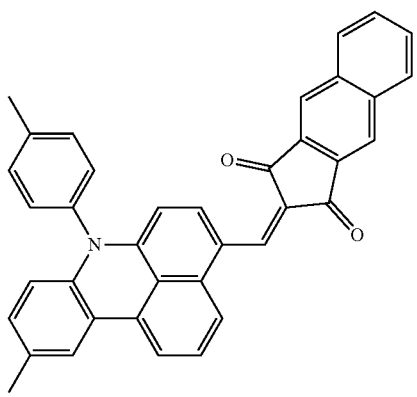

-continued

A4
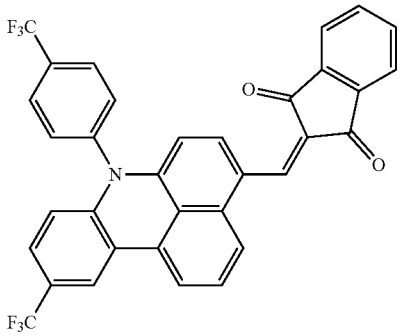

A5
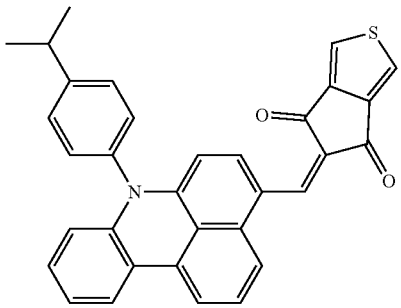

A6
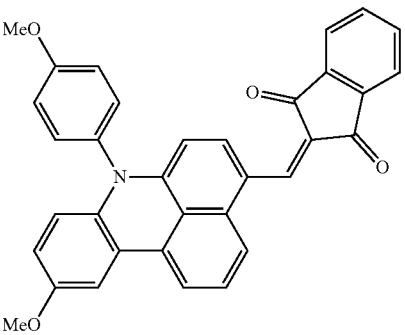

-continued
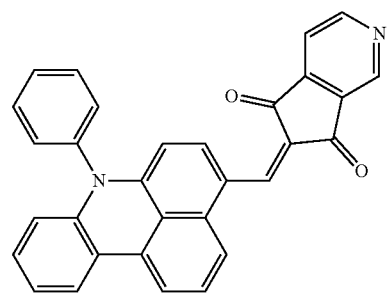
A7
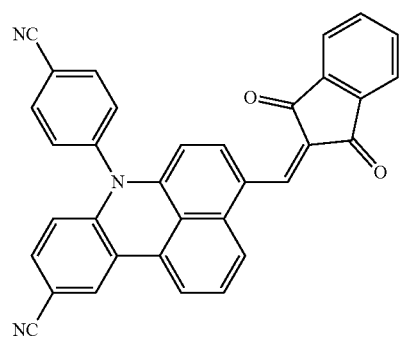
A8
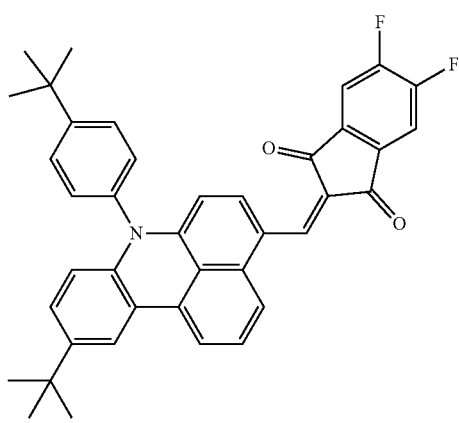
A9
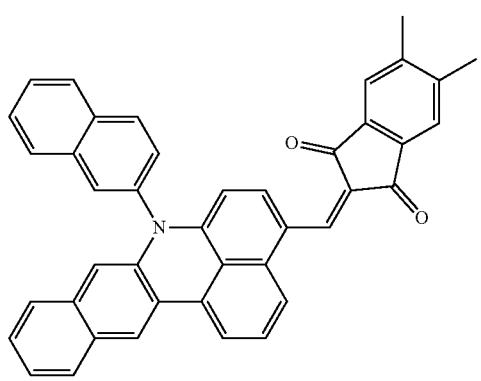
A10
-continued
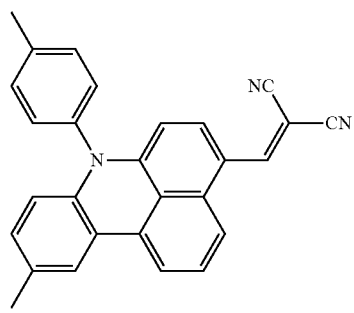
B1
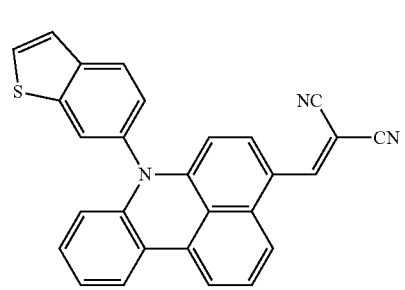
B2
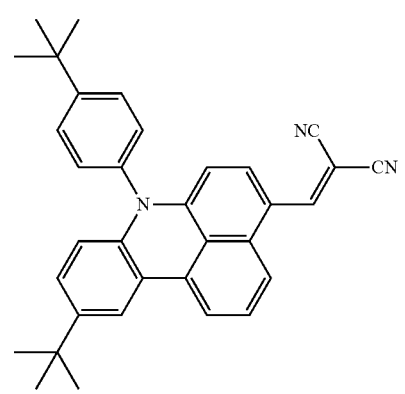
B3
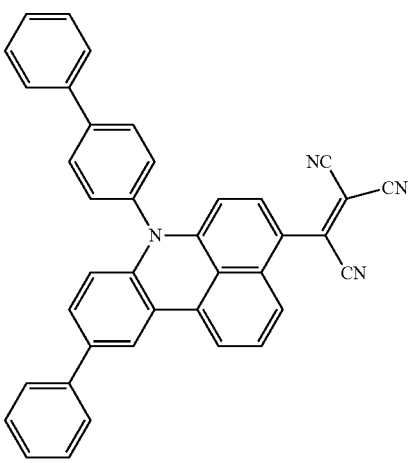
B4

B5
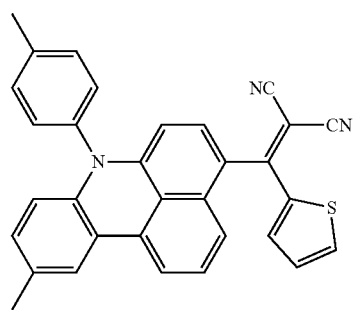
B6
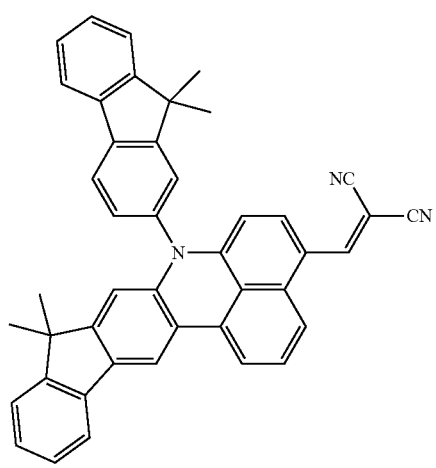
B7
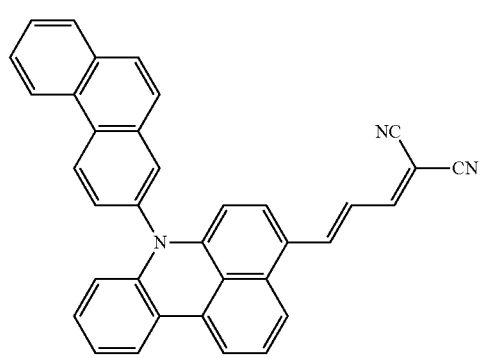
B8
B9
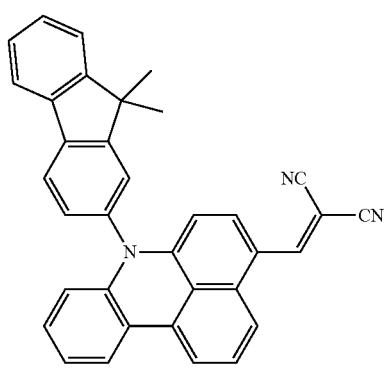
B10
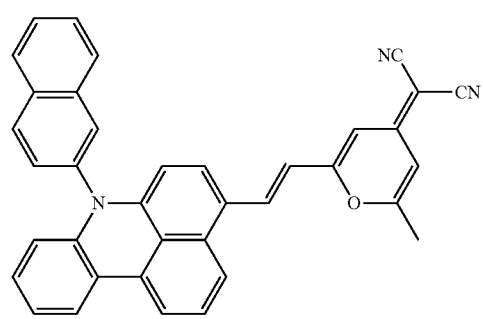
C1
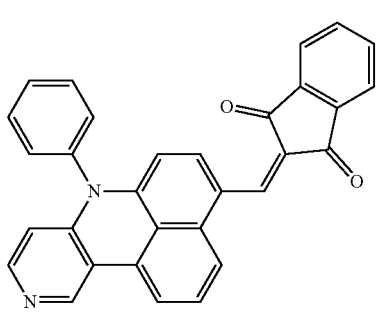
C2
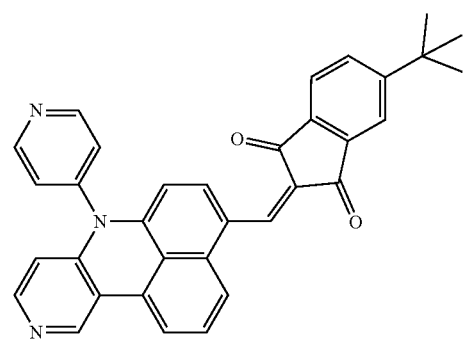

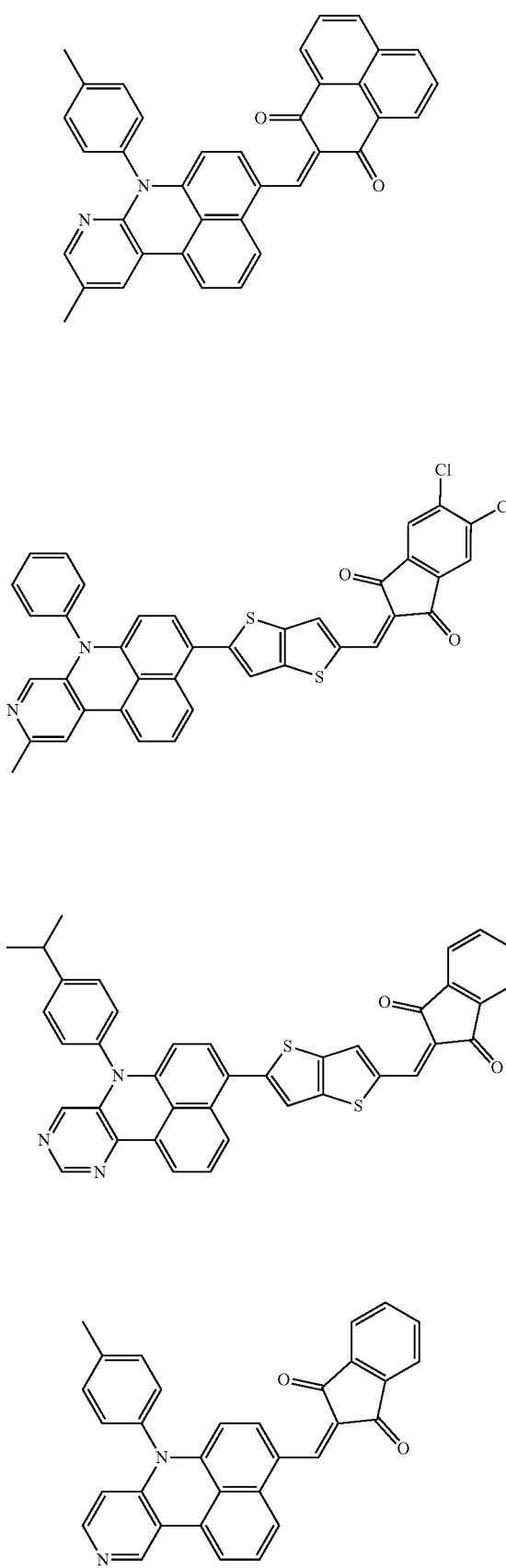
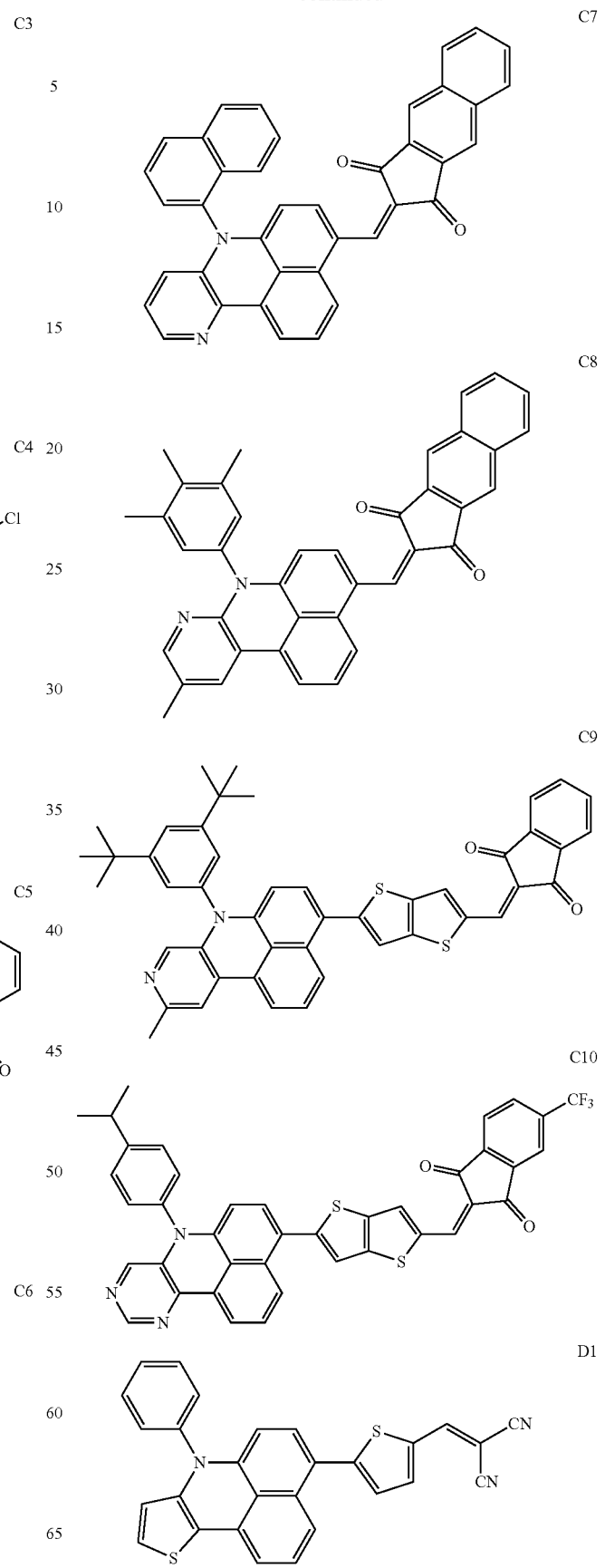

-continued
D2
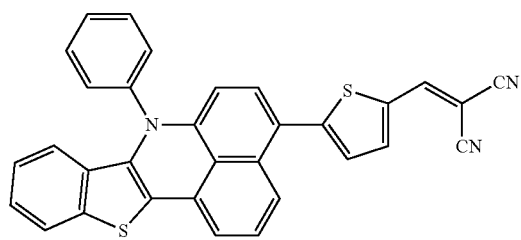
D3
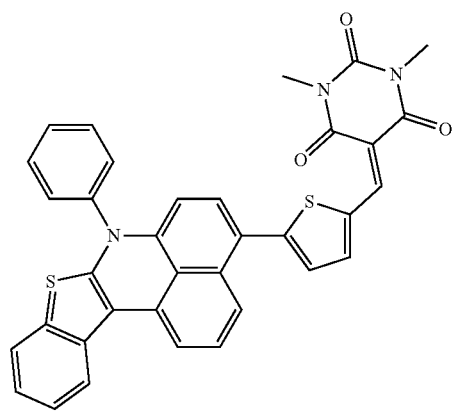
D4
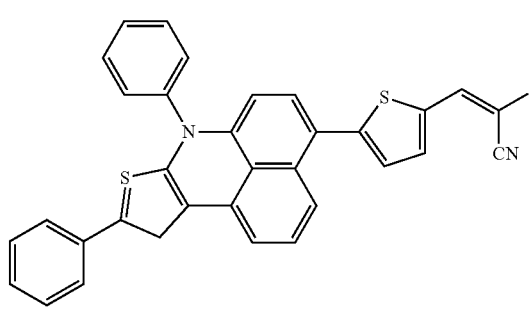
D5
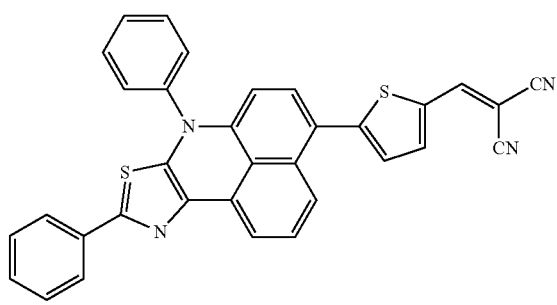
D6
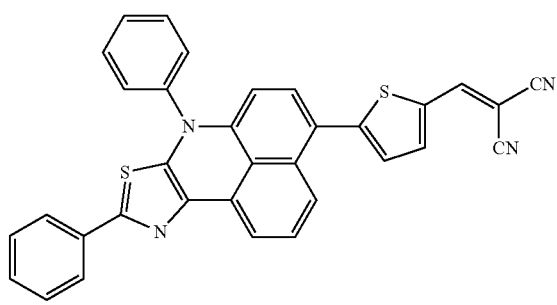
-continued
D7
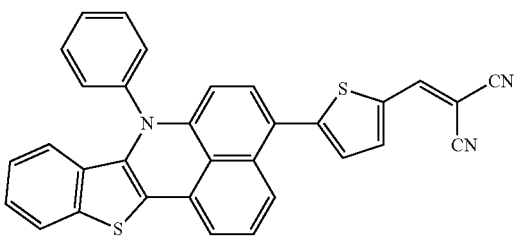
D8
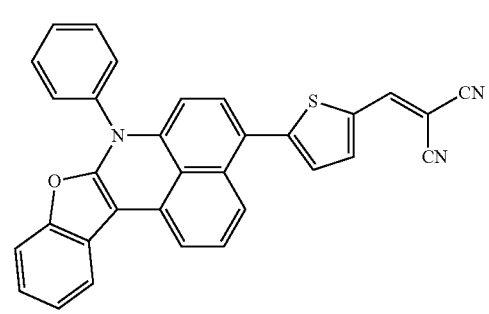
D9
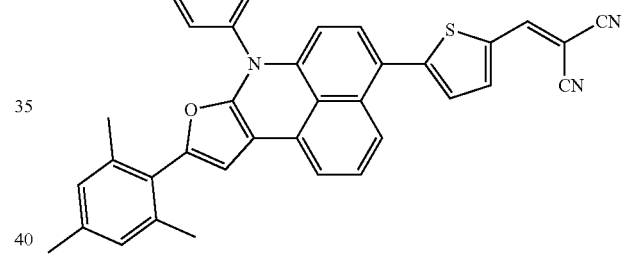
D10
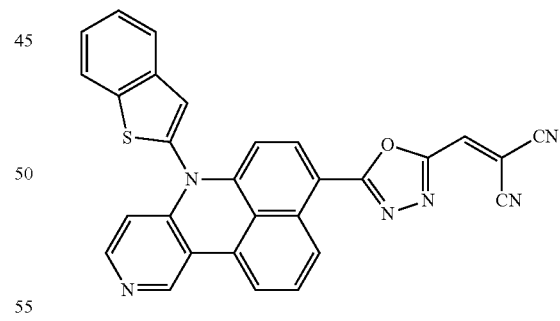
E1
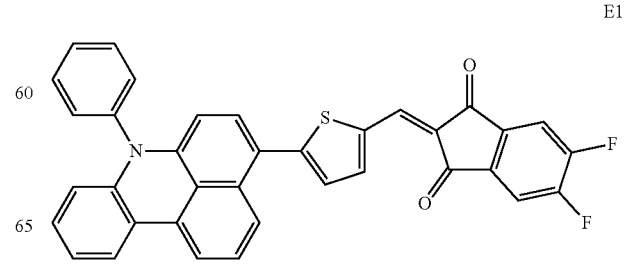

-continued
E2
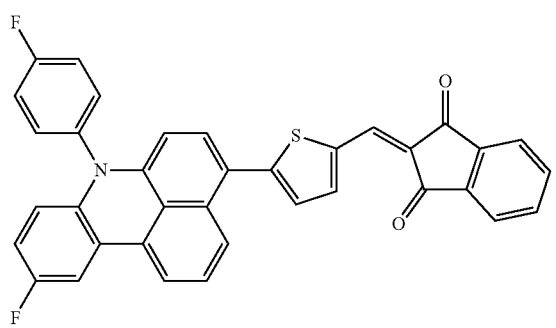
E3
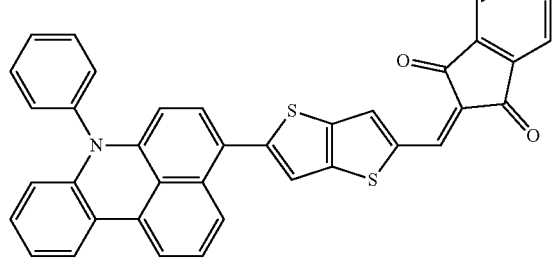
E4
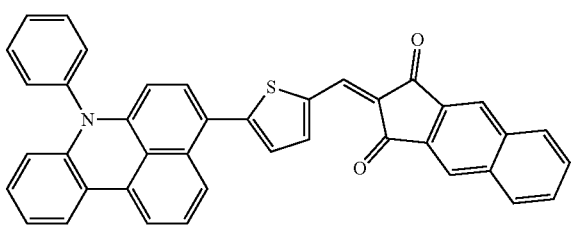
E5
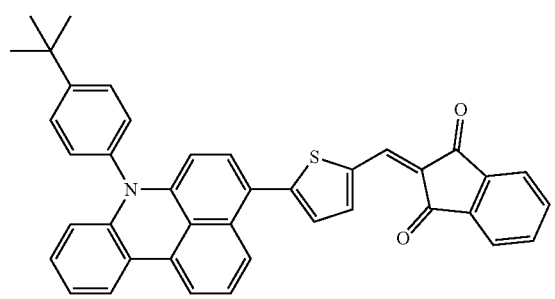
E6
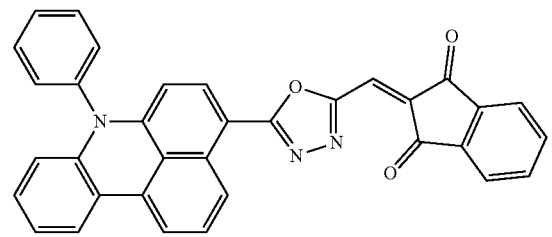
-continued
E7
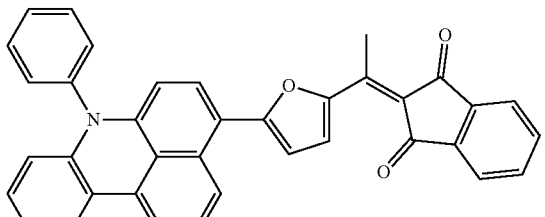
E8
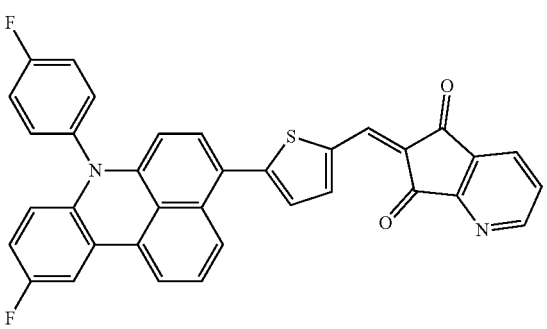
E9
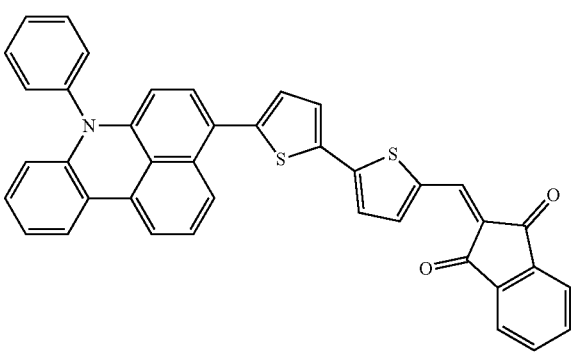
E10
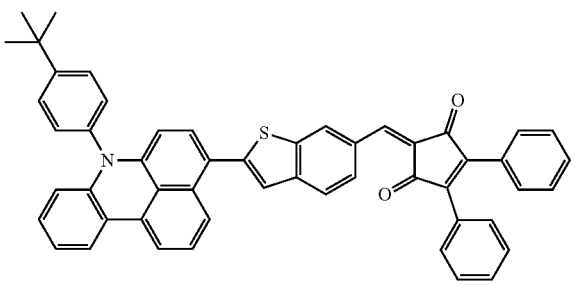
F1
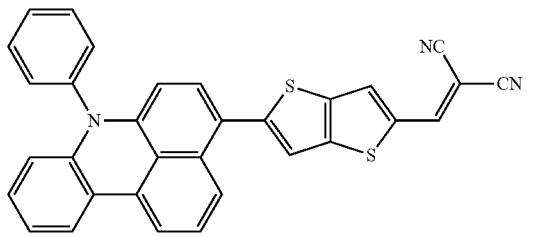

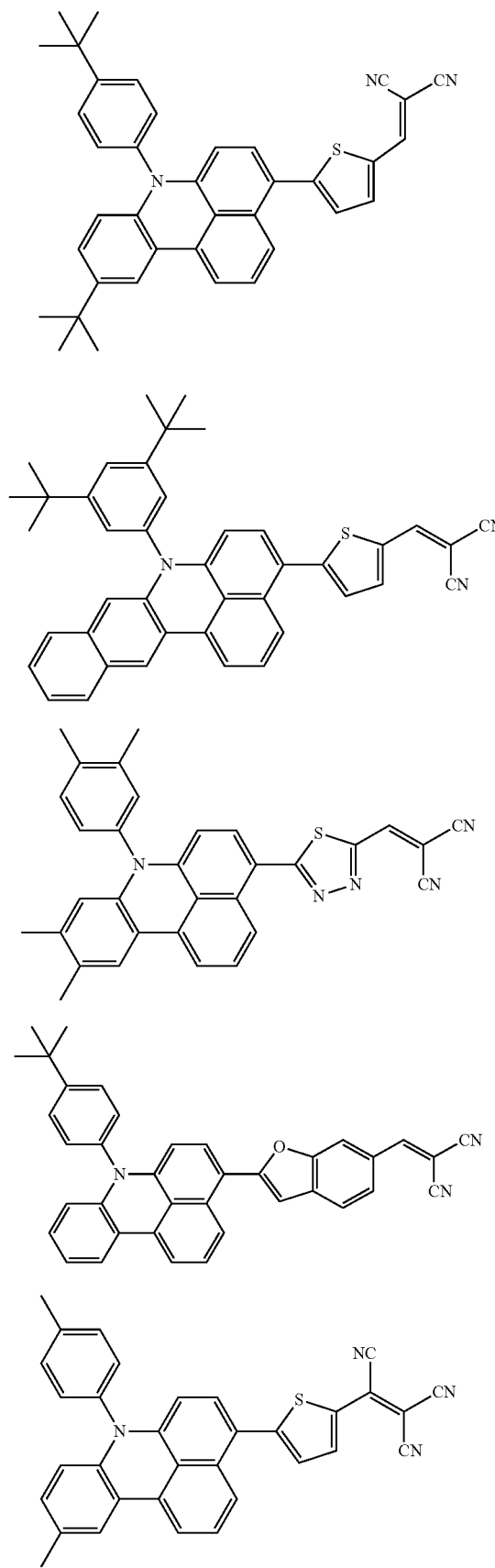
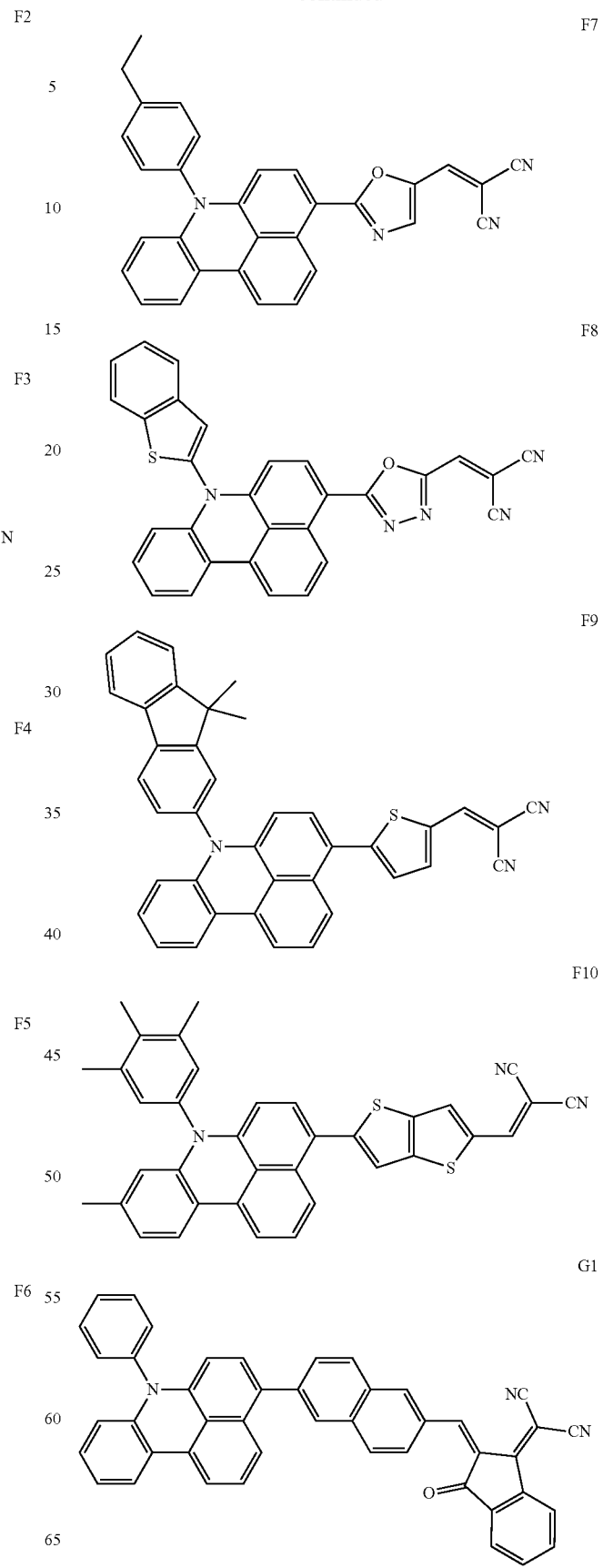

-continued
G2
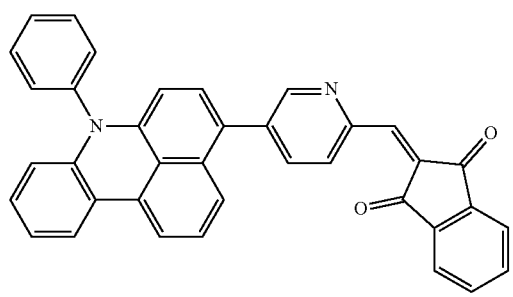
G3
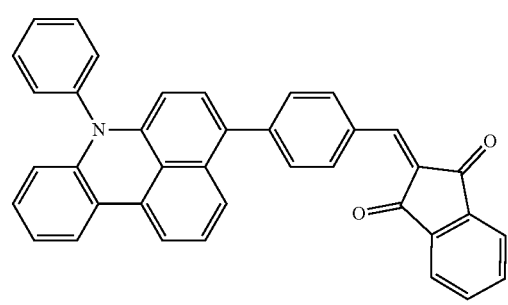
G4
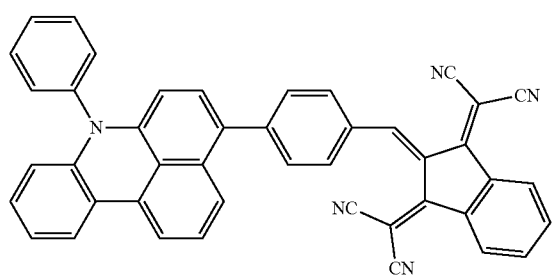
G5
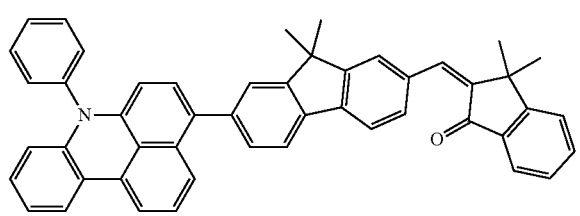
G6
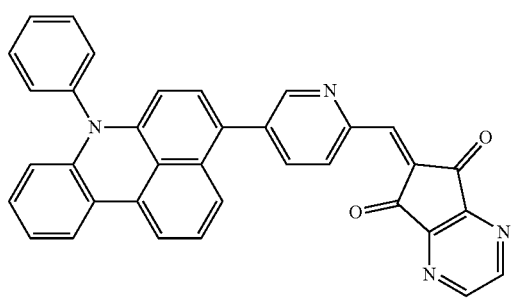
-continued
G7
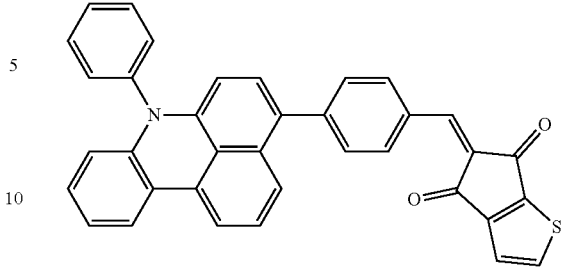
H1
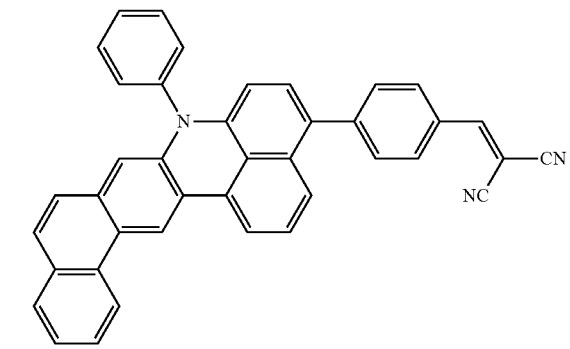
H2
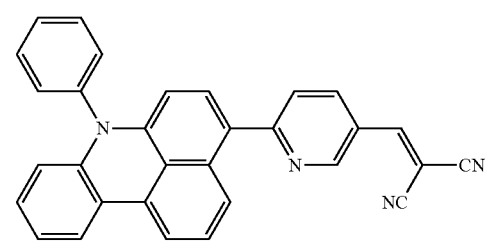
H3
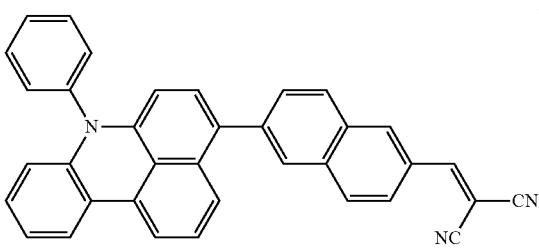
H4
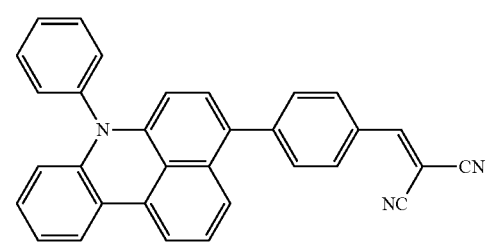

-continued

H5

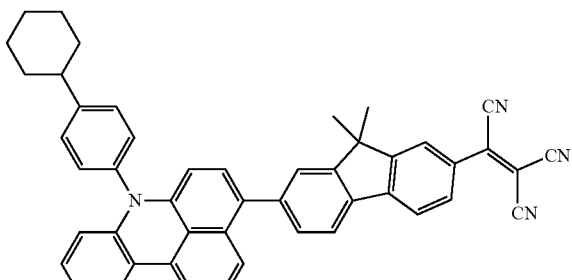

H6

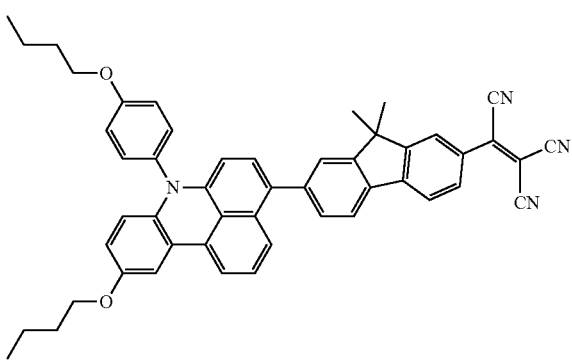

The compounds belonging to any group of A, B, E, F, G, and H of the exemplified compounds have a chemically stable aryl ring as the cyclic structure represented by A in general formula [1]. Accordingly, the compounds of these groups are thermally stable and highly sublimable.

The compounds belonging to either group C or D of the exemplified compounds have a heteroaryl ring as the cyclic structure represented by A in general formula [1]. These compounds have a heteroaryl ring at a part of the electron-rich skeleton and whose characteristics are changed by a large electronic effect. For example, a compound whose heteroaryl ring contains nitrogen has a high (deep) oxidation potential due to the high electronegativity of the nitrogen, accordingly being stable to oxidation. A compound whose heteroaryl ring contains sulfur or oxygen exhibits large intermolecular interaction due to the presence of many lone pairs of the sulfur or oxygen, exhibiting a high carrier-transporting ability. Hence, the compounds belonging to groups C and D are good in terms of stability or carrier-transporting ability resulting from an electronic effect.

The compounds belonging to any group of E, F, G, and H have an aryl ring as the cyclic structure represented by A in general formula [1] and in which m represents 1 or 2. Therefore, the absorption wavelength and the stability of the compound can be adjusted by the structure of $Ar_2$. For example, for the compounds belonging to groups E and F, whose $Ar_2$ has a 5-membered ring bound to the skeleton, $Ar_2$ does not much sterically repel the skeleton, and absorption resulting from CT transition is likely to occur. Thus, these compounds absorb light in a long wavelength region and have a high absorption coefficient. The compounds belonging to groups G and H, whose $Ar_2$ is aryl or pyridyl, are chemically stable.

The compounds belonging to groups A, C, E, and G are thermally stable because the electron-withdrawing substituent Q in formula [1] has the structure represented by formula [1-1]. Particularly when Q has a ring structure represented by any of formulas [3-1] to [3-9], the compound has a high glass transition temperature and easily forms a stable amorphous film.

The compounds belonging to groups B, D, F, and H are sublimable because Q in formula [1] is a low-molecular weight substituent represented by formula [1-2].

Production of the Organic Compound

A process for producing the organic compound of the present disclosure will now be described, but the organic compound may be produced in any other process.

The main skeleton of the organic compound of the present disclosure may be formed according to, for example, either the following synthesizing scheme [6-1] or [6-2]:

[6-1]

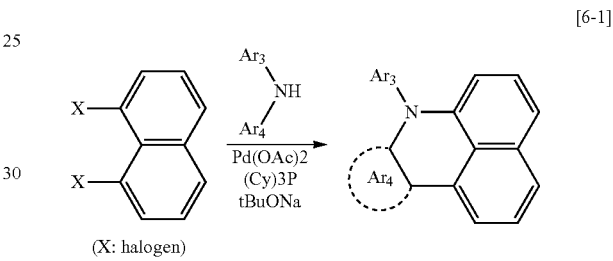

[6-2]

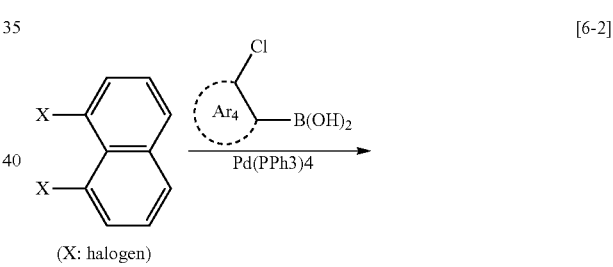

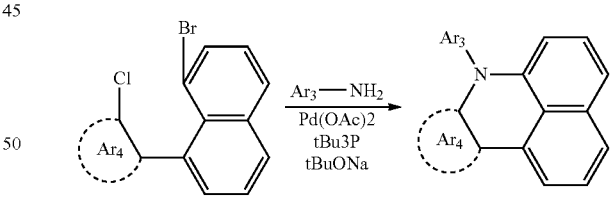

In Synthesizing Scheme [6-1], an amination reaction of a diarylamine with a dihalogen compound in the presence of a Pd catalyst is made simultaneously with a cyclization reaction to form the skeleton at one time. This scheme is advantageous in terms of easy synthesis.

In Synthesizing Scheme [6-2], $Ar_3$ and $Ar_4$ are synthesized step by step by a cross-coupling reaction in the presence of a Pd catalyst. This scheme is useful to produce a compound in which $Ar_3$ and $Ar_4$ have different structures.

Next, the resulting skeleton is brominated. The bromination of the skeleton may be made by a known reaction, and in which, for example, NBS may be used as the brominating agent as in the following Synthesis Scheme [7]:

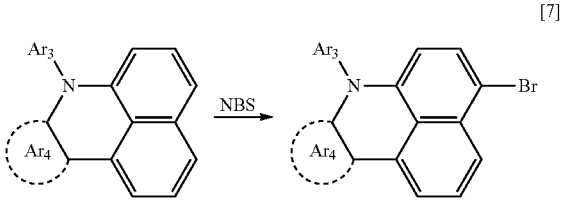

[7]

Next, a formyl group (ketone group) is introduced to the brominated skeleton by using n-butyllithium and dimethylformamide (DMF) as in Synthesizing Scheme [8-1] shown below. Alternatively, a formyl group (ketone group) may be introduced by a cross-coupling reaction of the brominated skeleton with an arylboronic acid in the presence of a Pd catalyst, as shown in the following Synthesizing Scheme [8-2]:

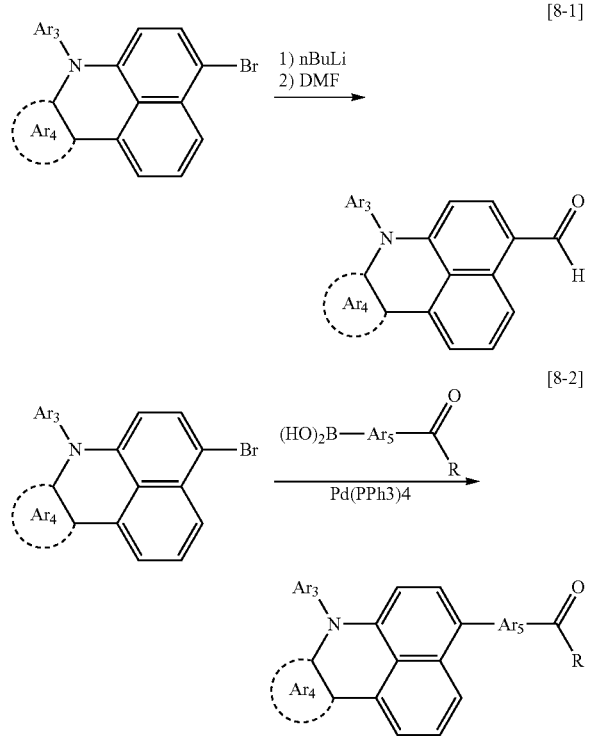

Finally, an electron-withdrawing substituent Q is introduced to the skeleton having the formyl group (ketone group) by Knoevenagel condensation as shown in the following Scheme [9], thus yielding an organic compound according to an embodiment of the present disclosure.

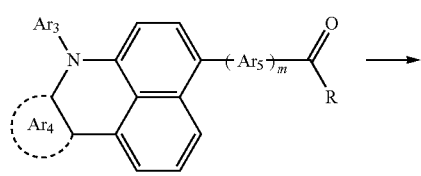

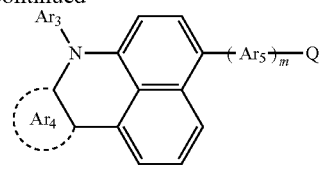

Photoelectric Conversion Element
1. Organic Photoelectric Conversion Element of the Present Disclosure
(1) Organic Photoelectric Conversion Element The photoelectric conversion element according to an embodiment of the present disclosure includes an electron collecting electrode, a hole collecting electrode, and at least one photoelectric conversion layer between the electron collecting electrode and the hole collecting electrode. The photoelectric conversion layer contains the organic compound represented by general formula [1] described above.

The organic compound of general formula [1] may be used in other layers or members as well as in the photoelectric conversion layer.

Figure 2:
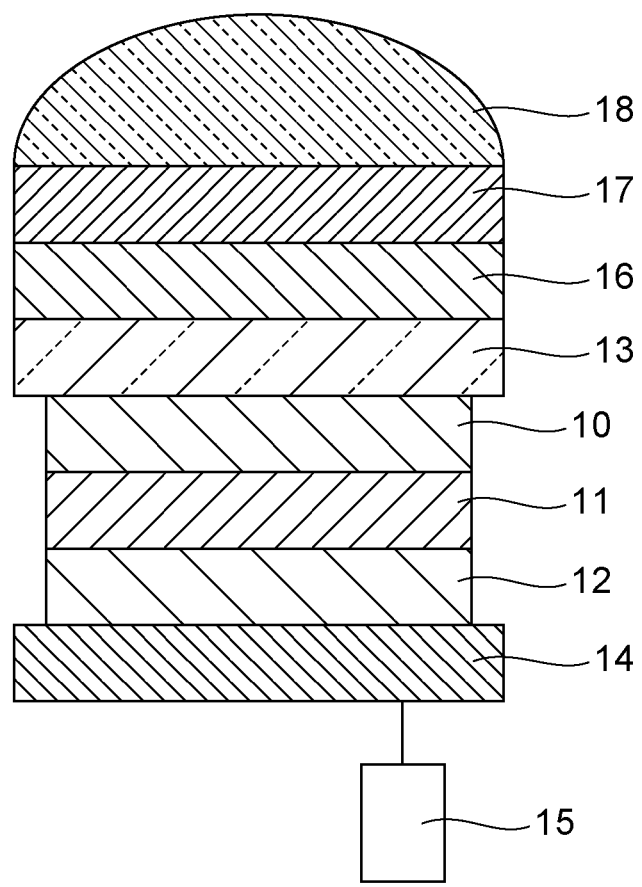
FIG. 2 is a schematic sectional view of a photoelectric conversion element containing an organic compound according to an embodiment of the present disclosure.

FIG. 2 is a schematic sectional view of the organic photoelectric conversion element according to an embodiment of the present disclosure. The organic photoelectric conversion element 1 shown in FIG. 2 includes a hole collecting electrode 13, and electron collecting electrode 14, and a multilayer structure between the hole collecting electrode 13 and the electron collecting electrode 14. The multilayer structure includes an electron blocking layer 10, a photoelectric conversion layer 11, and a hole blocking layer 12. Also, a protective layer 16 and a wavelength selection portion 17, and a microlens 18 are disposed over the hole collecting electrode 13. The electron collecting electrode 14 is connected to a readout circuit 15.

In the organic photoelectric conversion element 1 shown in FIG. 2, the photoelectric conversion layer 11 is an organic compound layer operable to convert light absorbed thereto into charges. In addition, the photoelectric conversion layer 11 is operable to transport the charges generated therein, that is, electrons and holes, to the electron collecting electrode 14 or the hole collecting electrode 13. The photoelectric conversion layer 11 may be defined by a single layer or may include a plurality of layers. The photoelectric conversion layer 11 may be a bulk-heterojunction layer (intermixed layer) containing a plurality of substances. In an embodiment, the photoelectric conversion element may include another photoelectric conversion layer in addition to the photoelectric conversion layer 11.

In the organic photoelectric conversion element 1 shown in FIG. 2, the hole collecting electrode 13 collects holes (charges) generated in the photoelectric conversion layer 11, and the electron collecting electrode 14 collects electrons (charges) generated in the photoelectric conversion layer 11. In the organic photoelectric conversion element 1 shown in FIG. 2, the electron collecting electrode 14 is disposed closer than the hole collecting electrode 13 to a pixel circuit, such as the readout circuit 15, while in another embodiment, the hole collecting electrode 13 may be disposed closer to the pixel circuit.

In the organic photoelectric conversion element 1 shown in FIG. 2, the electron blocking layer 10 restrains electrons from being injected into the photoelectric conversion layer 11 from the hole collecting electrode 13 and, in addition, transports holes to the hole collecting electrode 13 from the photoelectric conversion layer 11. The electron blocking layer 10 may be defined by a single layer or may include a plurality of layers. The electron blocking layer 10 may be an intermixed layer containing a plurality of substances.

In the organic photoelectric conversion element 1 shown in FIG. 2, the hole blocking layer 12 restrains hole from being injected into the photoelectric conversion layer 11 from the electron collecting electrode 14 and, in addition, transports electrons to the electron collecting electrode 14 from the photoelectric conversion layer 11. The hole blocking layer 12 may be defined by a single layer or may include a plurality of layers. The hole blocking layer 12 may be an intermixed layer containing a plurality of substances.

The multilayer structure disposed between the hole collecting electrode 13 and the electron collecting electrode 14 is not limited to the above-described three-layer structure composed of the electron blocking layer 10, the photoelectric conversion layer 11, and the hole blocking layer 12. For example, in an embodiment, an intervening layer may be disposed between the electron blocking layer 10 and the hole collecting electrode 13 or between the hole blocking layer 12 and the electron collecting electrode 14. The intervening layer is intended to increase the efficiency of injecting charges into the corresponding collecting electrode or to inhibit charges from being injected into the organic compound layers when a voltage is applied. The intervening layer, if formed, may be an organic compound layer containing an organic compound or an inorganic compound layer containing an inorganic compound.

In the organic photoelectric conversion element 1 shown in FIG. 2, the electron collecting electrode 14 is connected to the readout circuit 15. However, in another embodiment, the readout circuit 15 may be connected to the hole collecting electrode 13. The readout circuit 15 reads information according to charges generated from the photoelectric conversion portion layer 11 and transmits the information to, for example, a signal processing circuit disposed on the downstream side. The readout circuit 15 includes a transistor operable to output, for example, signals according to the charges generated from the organic photoelectric conversion element 1.

In the organic photoelectric conversion element 1 shown in FIG. 2, an inorganic protective layer 16 is disposed on the hole collecting electrode 13. The inorganic protective layer 16 is intended to protect the structure including the electron collecting electrode 14, the hole blocking layer 12, the photoelectric conversion layer 11, the electron blocking layer 10, and the hole collecting electrode 13 that are formed in this order.

In the organic photoelectric conversion element 1 shown in FIG. 2, the color filter 17 (wavelength selection portion) is disposed on the inorganic protective layer 16. The color filter 17 may transmit red light in the visible wavelength region. In an embodiment, color filters 17 may be provided one for each organic photoelectric conversion element or one for a plurality of organic photoelectric conversion elements. The color filters 17 may be arranged in a Bayer array defined by any two adjacent organic photoelectric conversion elements.

In the organic photoelectric conversion element 1 shown in FIG. 2, an optical member, such as a microlens 18, is disposed on the color filter 17. The microlens 18 is operable to concentrate incident light in the photoelectric conversion layer 11. In an embodiment, microlenses 18 may be provided one for each organic photoelectric conversion element or one for a plurality of organic photoelectric conversion elements. It may be beneficial to provide the microlenses one for each organic photoelectric conversion element.

For photoelectric conversion in the organic photoelectric conversion element, a voltage may be applied between the hole collection electrode 13 and the electron collecting electrode 14. The voltage applied between the two electrodes depends on the total thickness of the organic compound layers (the electron blocking layer 10, the photoelectric conversion layer 11, and the hole blocking layer 12) and may be, for example, in the range of 1 V to 15 V. In an embodiment, the voltage may be in the range of 2 V to 10 V.

(2) Photoelectric Conversion Layer

The photoelectric conversion layer of the organic photoelectric conversion element of the present disclosure will now be described. Beneficially, the photoelectric conversion layer exhibits a high optical absorptance and efficient charge separation of received light, hence having a high photoelectric conversion efficiency. Also, it is beneficial to rapidly transport charges (electrons and holes) to either collecting electrode. The photoelectric conversion layer may be made of a material having a high glass transition temperature from the viewpoint of reducing crystallization and other degradation of the layer. From the viewpoint of increasing the quality of the layer, the photoelectric conversion layer may be an intermixed layer containing a compound having a high glass transition temperature.

In an embodiment, the photoelectric conversion layer contains a p-type organic semiconductor or an n-type organic semiconductor. p-Type organic semiconductors are electron-donating and hole-transporting organic compounds, and n-type organic semiconductors are electron-acceptable and electron-transporting organic compounds. In an embodiment, the photoelectric conversion layer may be at least partially a bulk-heterojunction layer (intermixed layer) containing a p-type organic semiconductor and an n-type organic semiconductor. The photoelectric conversion layer that is a bulk heterojunction layer helps increase the photoelectric conversion efficiency (sensitivity) of the photoelectric conversion element. In addition, by mixing a p-type organic semiconductor with an n-type organic semiconductor in an appropriate ratio for forming the photoelectric conversion layer, the sensitivity distribution in the organic photoelectric conversion element associated with the maximum absorption wavelength of the photoelectric conversion layer and the optical response speed of the organic photoelectric conversion element associated with charge barrier and charge carrier mobility can be controlled as required. The photoelectric conversion layer is, beneficially, defined by a single layer but may include a plurality of layers.

In some embodiment, any of the compounds represented by general formula [1] may be used in the photoelectric conversion layer. The compound of general formula [1] is useful as the p-type organic semiconductor.

The n-type organic semiconductor may be a fullerene derivative. This is because fullerene derivatives are good for generating charges (holes and electrons) from excitons and transporting the charges and, in addition, have the function of absorbing visible light to generate excitons.

Fullerene, which is the skeleton common to the fullerene derivatives, refers to a general term of clusters in the form of a closed hollow shell composed of only a large number of carbon atoms. Exemplary fullerenes include C60 and higher-carbon-number structures, such as C70, C74, C76, and C78.

Fullerene derivatives are compounds formed by introducing a substituent, such as an alkyl group, an aryl group, or a heterocyclic group, to fullerene. In the following description, fullerene and fullerene derivatives may be collectively referred to as fullerenes (and fullerene or a fullerene derivative may be referred to as a fullerene) in some cases. Fullerene derivatives may be used singly or in combination.

In a fullerene, the fluoranthene skeletons of fullerene molecules stack on one another. Accordingly, the molecules of the organic compound, or the fullerene, can be aligned in a direction, thus forming a path of electrons to increase electron-transporting ability. Consequently, the response of the organic photoelectric conversion element is increased. The fullerene content in the photoelectric conversion layer may be in the range of 20% by volume to 80% by volume.

Examples of the fullerene or fullerene derivative that can be contained in the photoelectric conversion layer include Fullerene C60, Fullerene C70, Fullerene C76, Fullerene C78, Fullerene C80, Fullerene C82, Fullerene C84, Fullerene C90, Fullerene C96, Fullerene C240, Fullerene 540, mixed fullerenes, fullerene nanotubes, and the following fullerene derivatives:

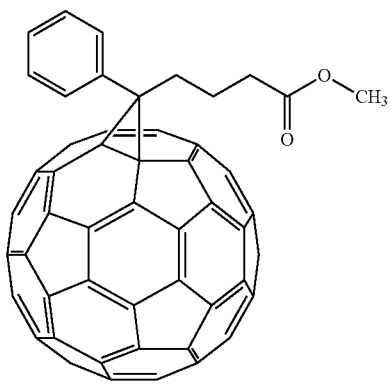

[60]PCBM

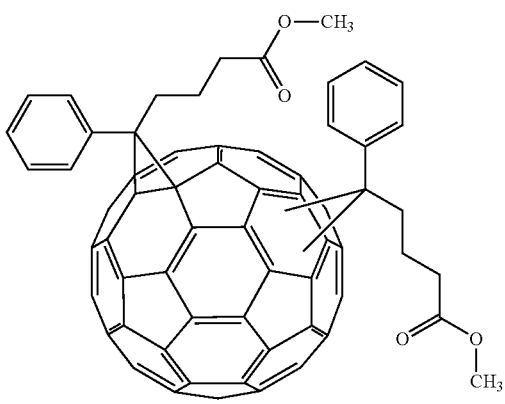

bis[60]PCBM

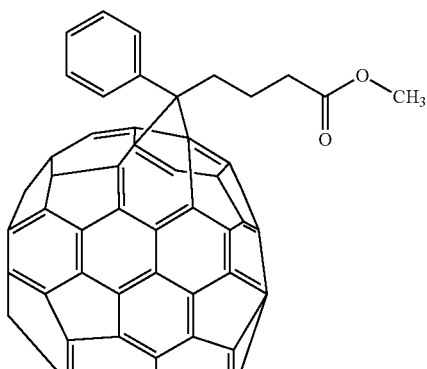

[70]PCBM

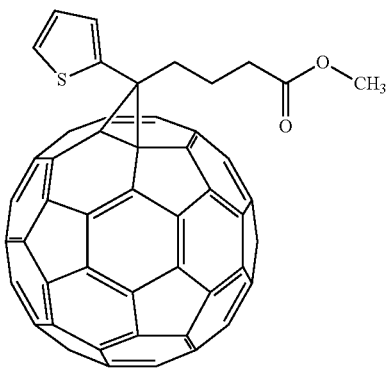

[60]ThCBM

In addition to the p-type organic semiconductor and the n-type organic semiconductor, the photoelectric conversion layer may contain other constituents. Other constituents include a charge transport/injection material acting to transport holes or electrons generated from the photoelectric conversion layer and immediately inject the charges to the corresponding collecting electrode and a film stabilizer acting to help the thermal stability of the organic compound layer and the formation of a uniform amorphous thin film.

(3) Electron Blocking Layer

The electron blocking layer of the organic photoelectric conversion element of the present disclosure will now be described. The electron blocking layer may have a low electron affinity (close to the vacuum level) from the viewpoint of preventing the injection of electrons into the photoelectric conversion layer from the hole collecting electrode. The material of the electron blocking layer may have a high hole mobility from the viewpoint of rapidly transporting holes generated from the photoelectric conversion layer to the hole collecting electrode. From the viewpoint of reducing crystallization and other degradation of the layer, the hole blocking material may have a high glass transition temperature. From the viewpoint of increasing the quality of the layer, the electron blocking layer may be an intermixed layer containing a material having a high glass transition temperature. Exemplary electron blocking materials include, but are not limited to, the following:

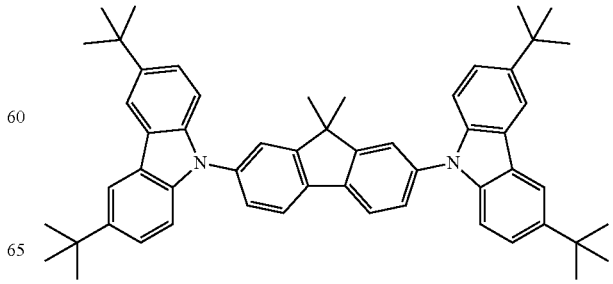

EB1

EB2

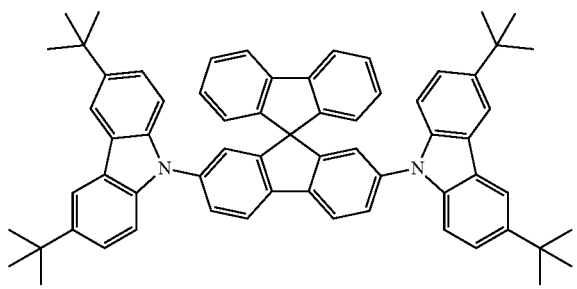

HB2

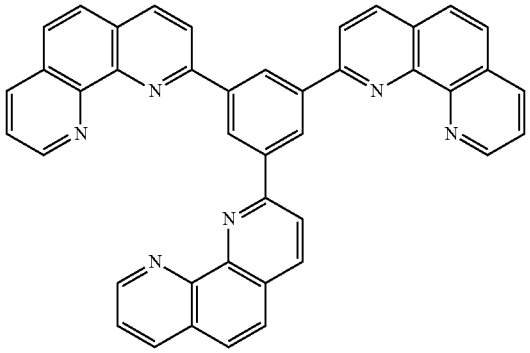

EB3

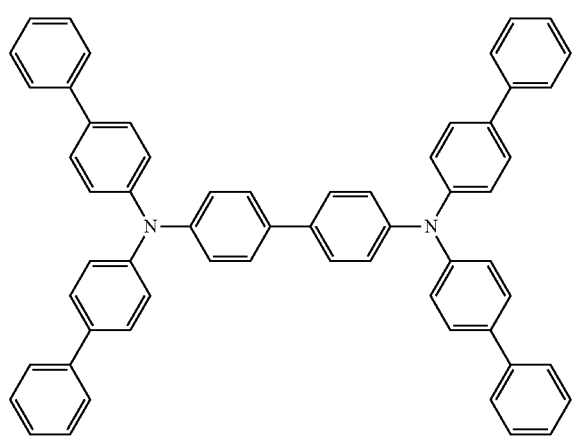

HB3

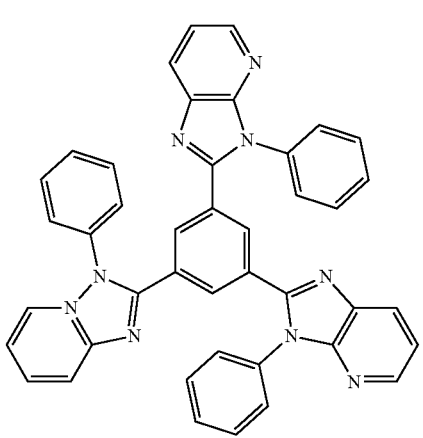

HB4

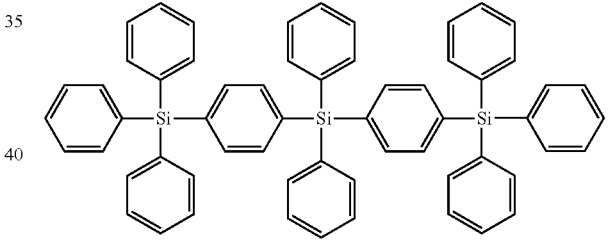

(4) Hole Blocking Layer

The hole blocking layer of the organic photoelectric conversion element of the present disclosure will now be described. The hole blocking layer may have a high ionization potential (distant from the vacuum level) from the viewpoint of preventing the injection of holes into the photoelectric conversion layer from the electron collecting electrode. The material of the hole blocking layer may have a high electron mobility from the viewpoint of rapidly transporting electrons generated from the photoelectric conversion layer to the electron collecting electrode. From the viewpoint of reducing crystallization and other degradation of the layer, the hole blocking material may have a high glass transition temperature. From the viewpoint of increasing the quality of the layer, the hole blocking layer may be an intermixed layer containing a material having a high glass transition temperature. Exemplary hole blocking materials include, but are not limited to, the following:

HB1

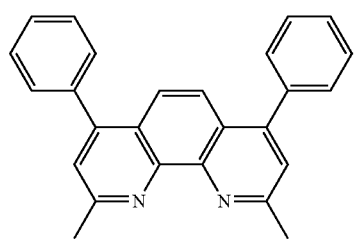

In addition to these compounds, fullerene derivatives that are well known as an n-type organic semiconductor may be used. Fullerene derivatives are good for transporting electrons as described above and may be used as a constituent of the hole blocking layer.

(5) Members Other than the Organic Compound Layers

Members of the organic photoelectric conversion element other than the organic compound layers will now be described.

(5-1) Substrate

The organic photoelectric conversion element according to the present disclosure may include a substrate, which is not shown in FIG. 2 though. The substrate may be a glass substrate, a flexible substrate, or the like.

The organic photoelectric conversion element may include a semiconductor substrate. The constituent elements of the semiconductor substrate are not limited, provided that a charge accumulation portion and a floating diffusion (FD) portion can be formed by impurity implantation. For example, the semiconductor may be Si, GaAs, GaP, or the like. In an embodiment, Si may be suitable.

The semiconductor substrate may be in the form of an n-type epitaxial layer. In this instance, a P-type well, an N-type well, a P-type semiconductor region, and an N-type semiconductor region are formed in the semiconductor substrate.

The charge accumulation portion is an N-type or a P-type semiconductor region formed in the semiconductor substrate by ion implantation and is operable to accumulate charges generated from the photoelectric conversion layer.

If the charge accumulation region accumulates electrons, an N-type semiconductor region may be formed at the surface of the semiconductor substrate, or an accumulation diode having a P—N structure may be formed from the surface of the semiconductor substrate. In either case, electrons are accumulated in the N-type semiconductor region.

If the charge accumulation region accumulates holes, a P-type semiconductor region may be formed at surface of the semiconductor substrate, or an accumulation diode having an N—P structure may be formed from the surface of the semiconductor substrate. In either case, holes are accumulated in the P-type semiconductor region.

Accumulated charges are transferred to the FD portion from the charge accumulation portion. This charge transfer may be controlled by a gate electrode. The charges generated from the photoelectric conversion layer are accumulated in the charge accumulation portion, and the charges accumulated in the charge accumulation portion are transferred to the FD portion. Then, the charges are converted into current by an amplifying transistor, which will be described herein later.

If the charge accumulation portion has a P—N junction, the photoelectric conversion may be made with light leaking from the photoelectric conversion portion.

(5-2) Hole Collecting Electrode

The hole collecting electrode is operable to collect holes of the charges generated from the photoelectric conversion layer. In an imaging element, the pixel electrode may act as the hole collecting electrode. The hole collecting electrode may be made of any material provided that the material is transparent and electrically conductive.

For example, the material of the hole collecting electrode may be a metal, a metal oxide, a metal nitride, a metal boride, an organic electroconductive compound, or a mixture of these materials. More specifically, examples of the hole collecting electrode material include electrically conductive metal oxides, such as antimony- or fluorine-doped tin oxides (ATO, FTO) and the like, tin oxide, zinc oxide, indium oxide, indium tin oxide (ITO), and indium zinc oxide; metals, such as gold, silver, chromium, nickel, titanium, tungsten, and aluminum and oxides, nitrides, and other electrically conductive compounds of these metals, such as titanium nitride (TiN); mixtures and multilayer composites using any of these metals with any of the electrically conductive metal oxides; electrically conductive inorganic materials, such as copper iodide and copper sulfide; and electrically conductive organic materials, such as polyaniline, polythiophene, and polypyrrole and maultilayer composites using any of these organic materials and ITO or titanium nitride. In some embodiments, the hole collecting electrode may be made of a compound selected from the group consisting of titanium nitride, molybdenum nitride, titanium nitride, and tungsten nitride.

(5-3) Electron Collecting Electrode

The electron collecting electrode is operable to collect electrons of the charges generated from the photoelectric conversion layer. In an imaging element, the pixel electrode may act as the electron collecting electrode. The electron collecting electrode may be disposed closer than the hole collecting electrode to the pixel circuit.

The electron collecting electrode may be made of any of the materials including ITO, indium zinc oxide, $SnO_2$, antimony-doped tin oxide (ATO), ZnO, aluminum-doped zinc oxide (AZO), gallium-doped zinc oxide (GZO), $TiO_2$, and fluorine-doped tin oxide (FTO).

The two above-described collecting electrodes (hole collecting electrode, electron collecting electrode) each may be formed by an appropriate process selected according to the material. For example, they may be formed by a wet process, such as printing or coating, a physical process, such as vapor deposition, sputtering, or ion plating, or a chemical process, such as CVD or plasma CVD.

If either electrode is formed of ITO, the ITO electrode may be formed by an electron beam method, sputtering, resistance heating vapor deposition, a chemical reaction method (for example, sol-gel method), coating with an indium tin oxide dispersion, or the like. In this instance, the resulting ITO electrode may be subjected to surface treatment, such as UV-ozone treatment or plasma treatment. If TiN is used for forming either collecting electrode, the TiN electrode may be formed by reactive sputtering or any other deposition. In this instance, the resulting TiN electrode may be subjected to annealing, UV-ozone treatment, or plasma treatment.

(5-4) Protective Layer

The protective layer, which is disposed over the electrodes, may be an insulating layer. The protective layer may be made of a single material or a plurality of materials. If a plurality of materials are used, the protective layer may be defined by a multilayer structure or a single layer containing a plurality of materials. Examples of the material of the protective layer include organic materials, such as resin, and inorganic materials, such as SiNx, SiOx, and $Al_2O_3$, wherein X represents the mole fraction.

The protective layer may be provided with a planarizing layer thereon. The planarizing layer in intended to prevent the color filter acting as a wavelength selector from being affected by the surface condition of the protective layer. The planarizing layer may be formed by any of the known processes including coating and vapor deposition. Chemical-mechanical polishing/planarization (CMP) or the like may be performed if necessary.

In an embodiment, the planarizing layer may be made of an organic material, such as resin, or an inorganic material, such as SiNx, SiOx, or $Al_2O_3$. In an embodiment, the planarizing layer may be made of an organic compound or a mixture of organic compounds.

(5-5) Color Filter Layer

The color filter is disposed over the planarizing layer. If the planarizing layer is not provided, the color filter is disposed on the protective layer. A color filter layer may be disposed on the side through which light enters the photoelectric conversion element.

The color filter transmits light having a predetermined wavelength more than light having other wavelengths. For example, by using three types of color filters for red (R), green (G), and blue (B) light, the entire region of visible wavelengths can be covered. When the three types of color filters are used, the R, G, and B color filters may be arranged in a Bayer array. As an alternative to the color filter, a prism capable of separating a light component having a predetermined wavelength or a scintillator may be used.

The position of the color filter layer is not limited to that shown in FIG. 2. The color filter or any other wavelength selection portion may be disposed at any position in the light path between the targeted object or the light source and the photoelectric conversion layer.

(5-6) Microlens

Microlenses are a type of optical member operable to concentrate external light in the photoelectric conversion layer. In the embodiment shown FIG. 2, the microlens is hemispherical but is not limited to such a shape.

The microlens may be made of, for example, quartz, silicon, or an organic resin. The microlens is not particularly limited in terms of shape and material provided that they do not interfere with condensing light.

The photoelectric conversion element may be combined with other photoelectric conversion elements disposed over an electrode. If photoelectric conversion elements operable to converting different wavelengths into electrical energy are combined, different wavelengths are detected at the same or substantially the same in-plane position over the substrate.

Alternatively, the photoelectric conversion element may further include one or more organic compound layers operable to convert light having a wavelength different from the light converted by the photoelectric conversion layer. The further organic compound layer(s) and the above-described photoelectric conversion layer may form a multilayer structure. Such a multilayer structure of organic compound layers enables light components having different wavelengths to be detected at the same or substantially the same position over the substrate as in the case of stacking a plurality of photoelectric conversion elements.

2. Applications of the Organic Photoelectric Conversion Element

The organic photoelectric conversion element according to the present disclosure may be used for light components having different wavelengths by appropriately selecting the material of the photoelectric conversion layer. In the case of using plural types of organic photoelectric conversion elements for different wavelengths in combination, by stacked these elements in the direction from the hole collecting electrode to the electron collecting electrode, an organic photoelectric conversion device is provided without using the color filter shown in FIG. 2. At least one type of the plural types of organic photoelectric conversion elements in the organic photoelectric conversion device is the organic photoelectric conversion element according to the present disclosure.

A two-dimensional, in-plane arrangement of the organic photoelectric conversion elements of the present disclosure may be used as a component of an optical area sensor. The optical area sensor includes a plurality of organic photoelectric conversion elements arranged in a matrix manner. The organic photoelectric conversion elements of the optical area sensor may be replaced with the above-described organic photoelectric conversion device.

The organic photoelectric conversion element of the present disclosure may be used as a component of an imaging device. The imaging device includes a plurality of organic photoelectric conversion elements each acting as a light-receiving pixel, and transistors each connected to one of the organic photoelectric conversion elements. The transistors used in this case refer to readout transistors operable to reading charges generated from the corresponding organic photoelectric conversion elements. The information based on the charges read by the transistor is transmitted to a sensor connected to the imaging device. The sensor may be a CMOS sensor, a CCD sensor, or the like. Pieces of information obtained by the light-receiving pixels are collected in the sensor, thus obtaining an image.

The imaging device may include optical filters, such as color filters, corresponding to each of the light-receiving pixels. If the organic photoelectric conversion elements are each for a specific color, it is beneficial that the color filters each transmit light having the specific color of the corresponding organic photoelectric conversion element. The color filters may be provided one for each light-receiving pixel or one for a plurality of light-receiving pixels.

The optical filter of the imaging device is not limited to a color filter and may be a low pass filter that transmits wavelengths other than those in the infrared region, a UV cut filter that transmits wavelengths other than those in the ultraviolet region, a long pass filter, or the like.

The imaging device may include an optical member such as microlenses corresponding to, for example, each of the light-receiving pixels. Each of the microlenses of the imaging device is a condenser lens that concentrates external light in the photoelectric conversion layer of the corresponding organic photoelectric conversion element. The microlenses may be provided one for each light-receiving pixel or one for a plurality of light-receiving pixels. If the imaging device has a plurality of light-receiving pixels, it is beneficial that each microlens be provided for a predetermined number (two or more) of light-receiving pixels.

The organic photoelectric conversion element of the present disclosure may be used in an imaging unit. The imaging unit includes an imaging optical system having a plurality of lenses, an imaging device operable to receive light that has passed through the imaging optical system, and an enclosure housing the imaging device. Alternatively, the imaging unit includes an enclosure having a joint section that can be connected to an imaging optical system. The imaging unit described herein may be a digital camera or a digital still camera.

The imaging unit may further include a signal receiver operable to receive a signal from the outside. The signal that the receiver receives is used for controlling at least the imaging range, imaging start point and imaging end point of the imaging unit. The imaging unit may further include a transmitter operable to transmit an obtained image to the outside. The imaging unit including the signal receiver and the transmitter may be used as a network camera.

Figure 3:
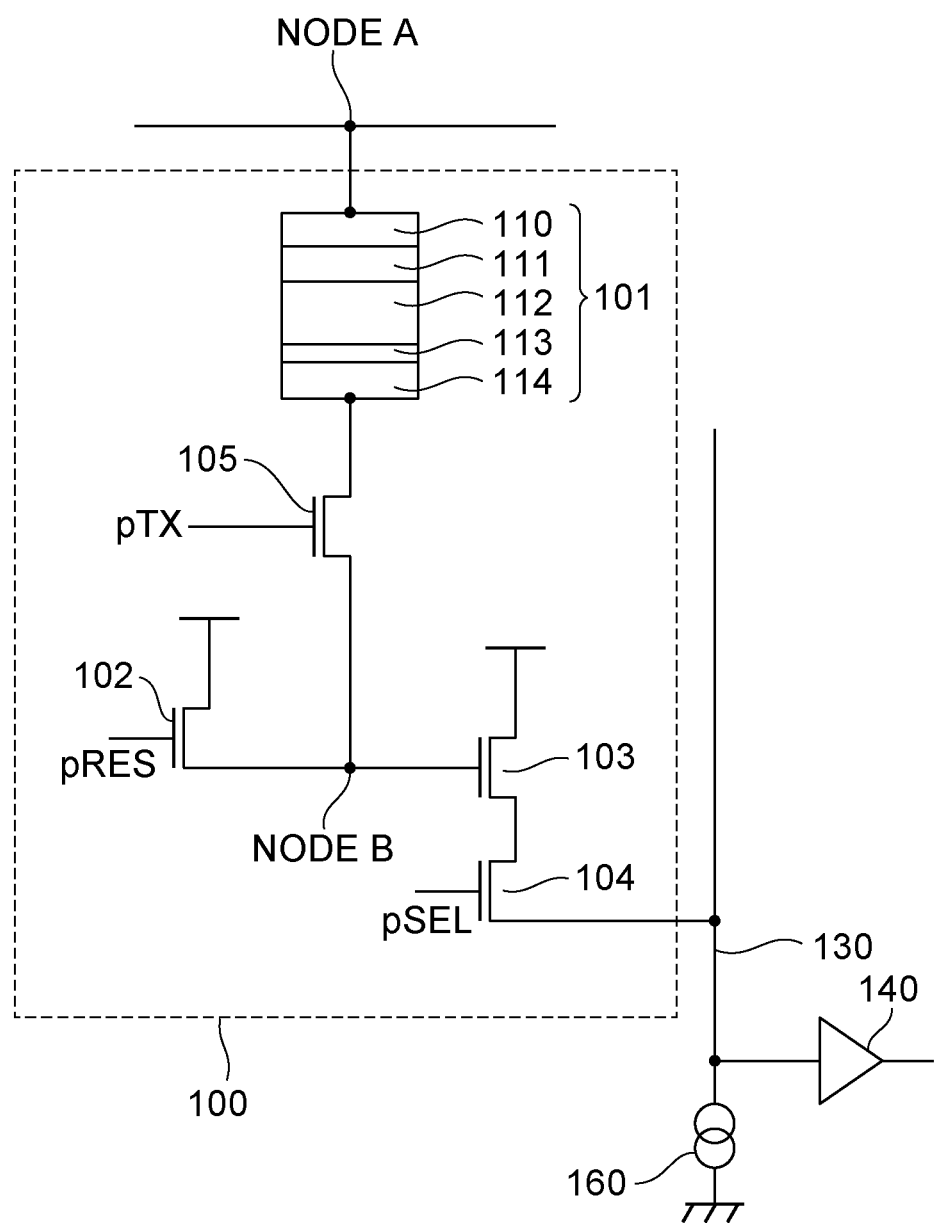
FIG. 3 is a schematic diagram of a drive circuit of a pixel including a photoelectric conversion element containing an organic compound according to an embodiment of the present disclosure.

FIG. 3 schematically illustrates a pixel 100 of a photoelectric conversion device according to an embodiment of the present disclosure. The photoelectric conversion portion 101 of the pixel 100 includes a hole collecting electrode (upper electrode) 110, an electron blocking layer 111, a photoelectric conversion layer 112, a hole blocking layer 113, and an electron collecting electrode (lower electrode) 114. The photoelectric conversion portion 101 defines a photodiode having a first terminal connected to a node A and a second terminal connected to a node B, as shown in FIG. 3.

In the embodiment shown in FIG. 3, the electron collecting electrode 114 of the photoelectric conversion portion 101 is connected to the node B with a transfer transistor 105 therebetween. The node B is connected to the gate electrode of an amplifying transistor 103. The node B is also connected to the source electrode of a reset transistor 102 that is a reset element. The source electrode, which is defined by an N+ impurity diffusion region formed in a P-type semiconductor substrate, defines a floating diffusion portion (hereinafter referred to as the FD portion). The P-type semiconductor substrate is set to a potential of GND (0 V). The signal charges accumulated in the FD portion are converted into voltage signals. A reset voltage is applied to the drain electrode of the reset transistor 102. The reset transistor 102 is switched on or off by reset control pulses pRES. On switching the reset transistor 102 on, a reset voltage is applied to the node B. The transfer transistor 105 is switched on or off by switching control pulses pTX.

The gate electrode of the amplifying transistor 103 acts as the input node of an amplifying portion. Thus, an amplifier amplifies signals from the photoelectric conversion portion 101. Thus, in the present embodiment, the pixel circuit that receives signals based on the signal charges generated by photoelectric conversion includes an amplifying portion.

A power-supply voltage is applied to the drain electrode of the amplifying transistor 103. The source electrode of the amplifying transistor 103 is connected to an output line 130 with a selection transistor 104 therebetween. The output line 130 is connected to a current source 160. The amplifying transistor 103 and the current source 160 define a pixel source follower circuit that outputs voltage signals to the output line 130 from the FD portion accumulating signal charges generated from the photoelectric conversion portion 101. The output line 130 is further connected to a column circuit 140. The signals output to the output line 130 from the pixel 100 are input to the column circuit 140.

Figure 4:
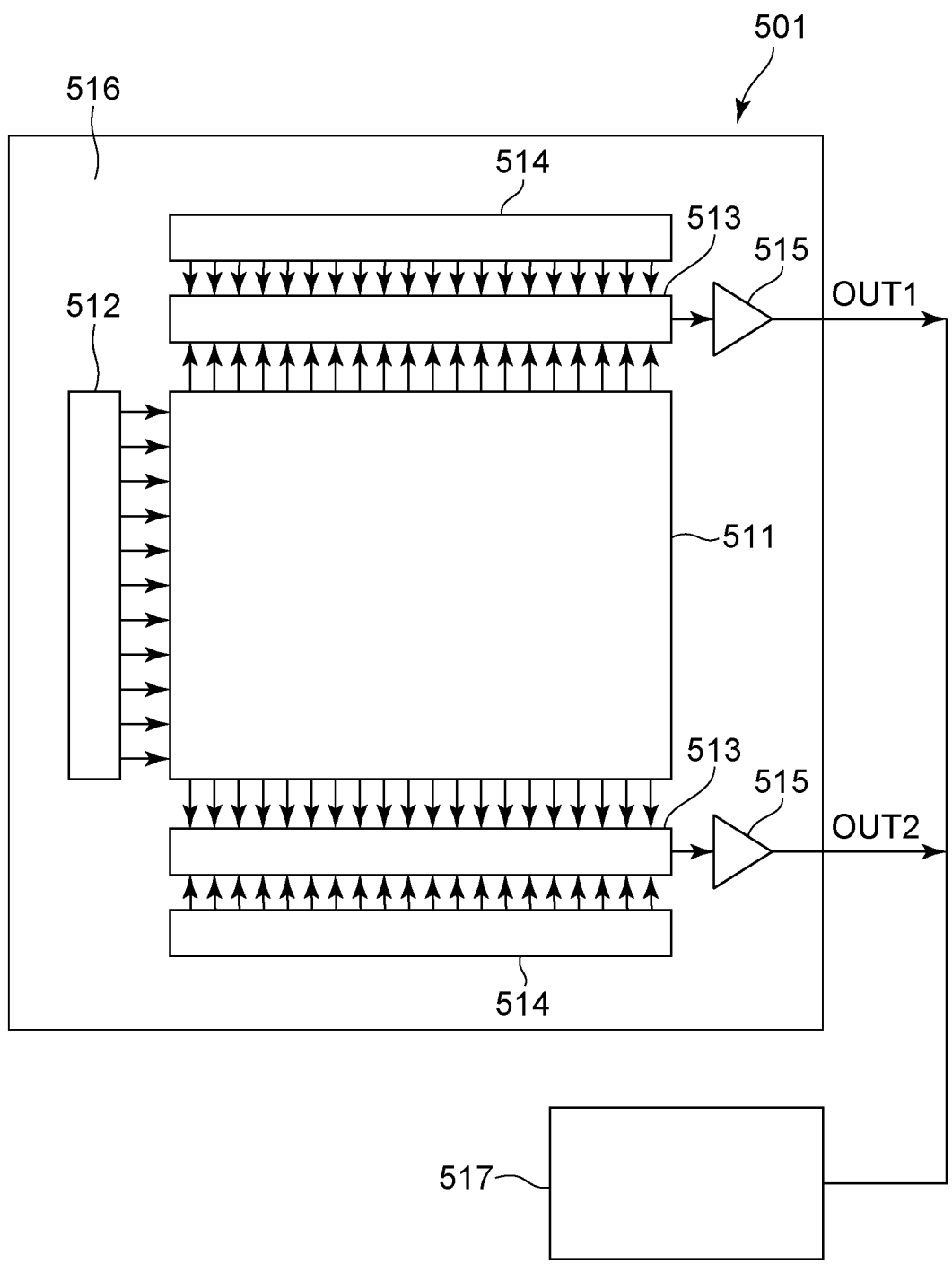
FIG. 4 is a schematic diagram of a peripheral circuit including a photoelectric conversion element containing an organic compound according to an embodiment of the present disclosure.

FIG. 4 is a diagram of an imaging device according to an embodiment of the present disclosure. The imaging device 501 has an imaging region 511 in which a plurality of pixels are two-dimensionally arranged, and a peripheral region 516. The peripheral region 516 is defined by the region other than the imaging region 511. The peripheral region 516 has a vertical scanning circuit 512, readout circuits 513, horizontal scanning circuits 514, and output amplifiers 515. The output amplifiers 515 are each connected to a signal processing portion 517. The signal processing portion 517 processes signals according to information read into the readout circuit and may be a CCD circuit or a CMOS circuit.

The readout circuits 513 each include, for example, a column amplifier, a CDS circuit, and an adder and perform amplification and addition of the signals read from the pixels in a row selected by the vertical scanning circuit 512 through the vertical signal lines. The column amplifier, the CDS circuit, the adder, and the like each may be provided one for each pixel line or one for a plurality of pixel lines. The horizontal scanning circuits 514 each generate signals for reading signals from the corresponding readout circuit 513 one after another. The output amplifiers 515 each amplify the signals in a row selected by the corresponding horizontal scanning circuit 514 and output the amplified signals.

The configuration just described is merely one of the exemplary embodiments of the photoelectric conversion device, and other configurations may be implemented in other embodiments. The readout circuits 513, the horizontal scanning circuits 514, and the output amplifiers 515 are each disposed, one each, at an upper and a lower region with the imaging region 511 therebetween, thus establishing two output paths. In another embodiment, however, three or more output paths may be established. The signals output from the output amplifiers 515 are synthesized into an image signal in the signal processing portions 517.

EXAMPLES

The subject matter of the present disclosure will be further described with reference to Examples. However, it should be appreciated that the subject matter of the present disclosure is not limited to the following Examples.

Example 1: Synthesis of Exemplified Compound A1

Exemplified Compound A1 was synthesized according to the following scheme:

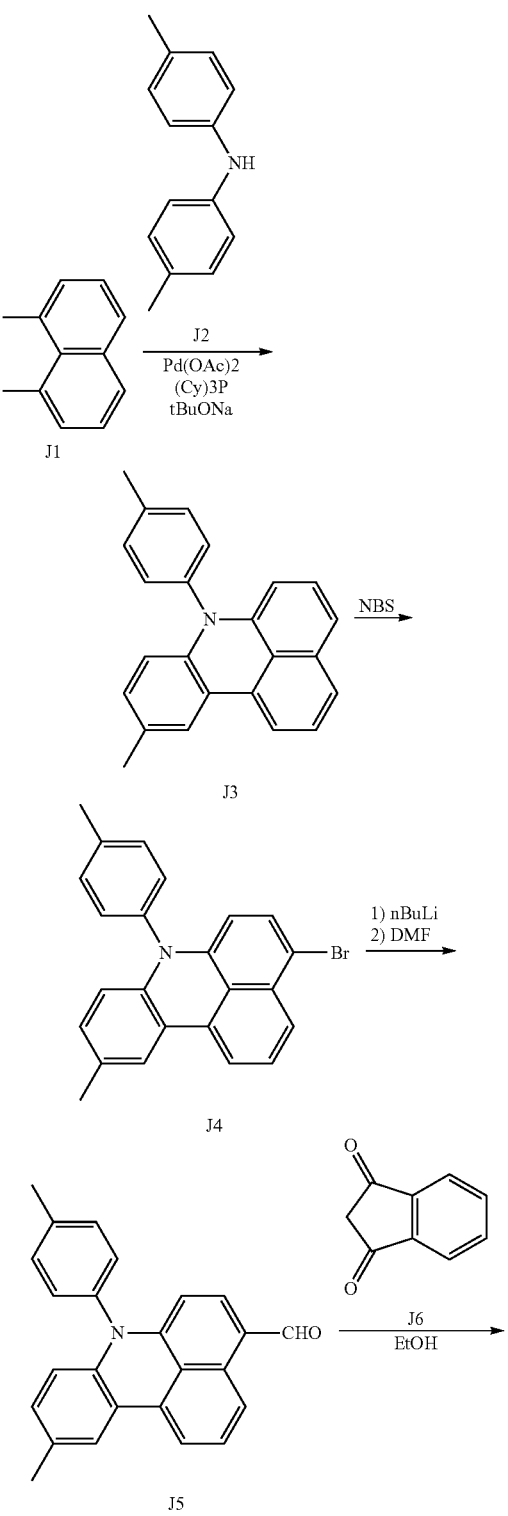

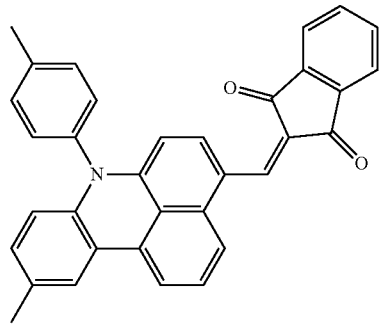

A1

(1) Synthesis of Compound J3
The following regents and solvent were added into a 300 mL flask:
Compound J1: 2.00 g (6.98 mmol)
Compound J2: 1.38 g (6.98 mmol)
Palladium acetate: 0.10 g (0.36 mmol)
Tricyclohexylphosphine: 0.20 g (0.70 mmol)
Sodium tert-butoxide: 2.01 g (21 mmol)
Dehydrated toluene: 70 mL Next, the resulting reaction solution was heated to reflux for 7 hours with stirring in a nitrogen atmosphere. After the reaction, the solution was passed through a membrane filter to yield a filtrate. Then, the filtrate was washed with water, dehydrated with sodium sulfate, and concentrated under reduced pressure to yield a crude product. Subsequently, the crude product was purified by silica gel chromatography (eluent: toluene/heptane=1/4) to yield 1.50 g of Compound J3 (yield: 67%).

(2) Synthesis of Compound J4
The following regent and solvent were added into a 100 mL flask:
Compound J3: 1.50 g (4.67 mmol)
Dehydrated DMF: 60 mL Subsequently, 0.83 g (4.67 mmol) of NBS was added to the resulting reaction solution with ice cooling and stirring in a nitrogen atmosphere. Then, the mixture was stirred for 1 hour at room temperature. After the reaction, the reaction solution was poured into 240 mL of water, followed by extraction with ethyl acetate. The organic phase thus obtained was dehydrated with sodium sulfate and was subsequently concentrated under reduced pressure to yield a crude product. Subsequently, the crude product was purified by silica gel chromatography (eluent: toluene/heptane=1/10) to yield 0.93 g of Compound J4 (yield: 50%).

(3) Synthesis of Compound J5
The following regent and solvent were added into a 100 mL flask:
Compound J4: 0.90 g (2.33 mmol)
Dehydrated THF: 20 mL Into the resulting reaction solution was dropped 1.50 mL (3.50 mmol) of 1.6 M solution of n-butyllithium in n-hexane with stirring at −80° C. in a nitrogen atmosphere, followed by stirring for 1 hour. Subsequently, 0.35 mL (4.66 mmol) of dehydrated DMF was dropped into the reaction solution, followed by heating slowly to room temperature. After the reaction, the reaction solution was poured into 100 mL of 1 N HCl aqueous solution, followed by extraction with ethyl acetate. The organic phase thus obtained was dehydrated with sodium sulfate and was subsequently concentrated under reduced pressure to yield a crude product. Subsequently, the crude product was purified by silica gel chromatography (eluent: toluene/heptane=1/1) to yield 0.33 g of Compound J5 (yield: 41%).

(4) Synthesis of Compound A1
The following regents and solvent were added into a 100 mL flask:
Compound J5: 0.27 g (0.77 mmol)
Compound J6: 0.17 g (1.16 mmol)
Ethanol: 20 mL Next, the resulting reaction solution was heated to reflux for 7 hours with stirring in a nitrogen atmosphere. After the reaction, the resulting liquid was passed through a membrane filter to yield a crude product. Subsequently, the crude product was purified by silica gel chromatography (eluent: toluene/heptane=1/4) to yield 0.25 g of Compound A1 (yield: 70%).

Compound A1 thus produced was identified by matrix-assisted laser desorption/ionization time-of-flight mass spectrometry (MALDI-TOF-MS) using Autoflex LRF manufactured by Bruker.
Measured value: m/z=477.55, Calculation value: $C_{34}H_{23}NO_2$=477.11
UV/visible absorption spectrum measurement The absorption spectrum was obtained by measuring a chloroform solution of the compound prepared in a quartz cell with a spectrophotometer V-560 manufactured by JASCO Corporation. The maximum absorption wavelength (λmax) was 615 nm.

Examples 2 to 6

Exemplified Compounds were synthesized and purified in the same manner as in Example 1 except that Organic Compound J2 was replaced with a diarylamine compound shown in the following Table 2 and Organic Compound J6 was replaced with an electron-withdrawing compound shown in Table 2. The resulting compound was identified by mass spectrometry as in Example 1. The results are shown in Table 2.

TABLE 2

|  | Compound J2 | Compound J6 | Exemplified Compound | Mass analysis results |
| --- | --- | --- | --- | --- |
| Example 2 | (structure) | (structure) | A3 | Measurement (m/z): 527.80 Calculation value $C_{38}H_{25}NO_2$: 527.61 |

TABLE 2-continued

| | Compound J2 | Compound J6 | Exemplified Compound | Mass analysis results |
|---|---|---|---|---|
| Example 3 | (2-naphthyl)(2-naphthyl)amine | 5,6-dimethyl-indane-1,3-dione | A10 | Measurement (m/z): 577.51<br>Calculation value $C_{42}H_{27}NO_2$: 577.67 |
| Example 4 | bis(4-tert-butylphenyl)amine | 5,6-difluoro-indane-1,3-dione | A9 | Measurement (m/z): 597.50<br>Calculation value $C_{40}H_{33}F_2NO_2$: 597.69 |
| Example 5 | diphenylamine | pyridine-fused cyclopentanedione | A7 | Measurement (m/z): 450.58<br>Calculation value $C_{31}H_{18}N_2O_2$: 450.49 |
| Example 6 | di(pyridin-4-yl)amine | 5-tert-butyl-indane-1,3-dione | C2 | Measurement (m/z): 507.54<br>Calculation value $C_{34}H_{25}N_3O_2$: 507.38 |

Example 7: Synthesis of Exemplified Compound B1

Exemplified Compound B1 was synthesized according to the following scheme:

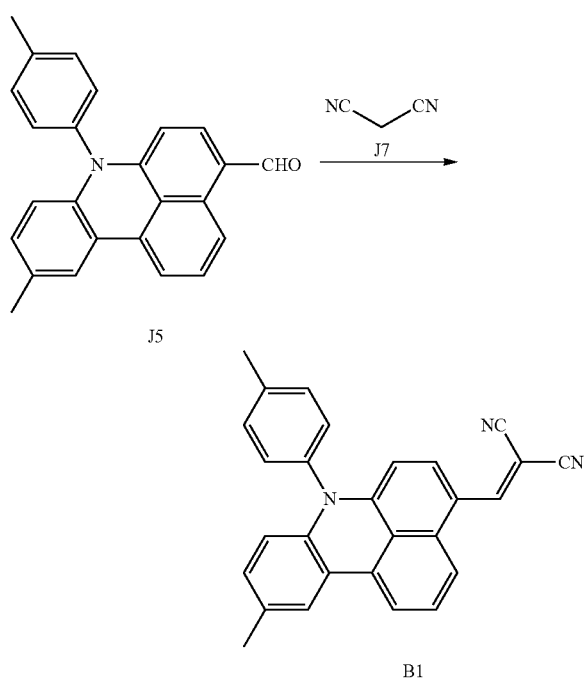

(1) Synthesis of Compound B1

The following regents and solvent were added into a 100 mL flask:

Compound J5: 0.27 g (0.77 mmol)

Compound J7: 0.17 g (1.16 mmol)

Dichloromethane: 20 mL

Triethylamine: several drops

Next, the reaction solution was stirred at room temperature for 7 hours in a nitrogen atmosphere. After the reaction, the resulting liquid was passed through a membrane filter to yield a crude product. Subsequently, the crude product was purified by silica gel chromatography (eluent: toluene/heptane=1/4) to yield 0.25 g of Compound B1 (yield: 70%). The resulting compound was identified by mass spectrometry as in Example 1.

Measured value: m/z=397.65, Calculation value: $C_{28}H_{19}N_3$=397.47

Example 8: Synthesis of Exemplified Compound B6

An exemplified compound was synthesized in the same manner as in Example 7 except that Organic Compound J5 was replaced with Organic Compound J8, followed by purification. The resulting compound was identified by mass spectrometry as in Example 1.

Measured value: m/z=601.95, Calculation value: $C_{44}H_{31}N_3$=601.74

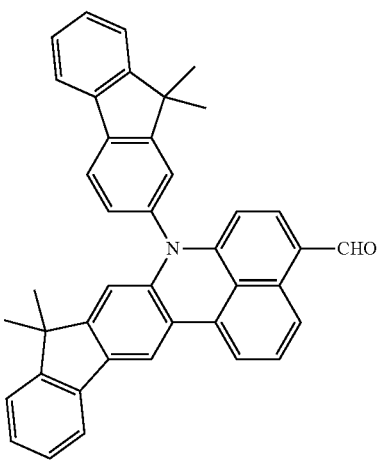

Example 9: Synthesis of Exemplified Compound F2

Exemplified Compound F2 was synthesized according to the following scheme:

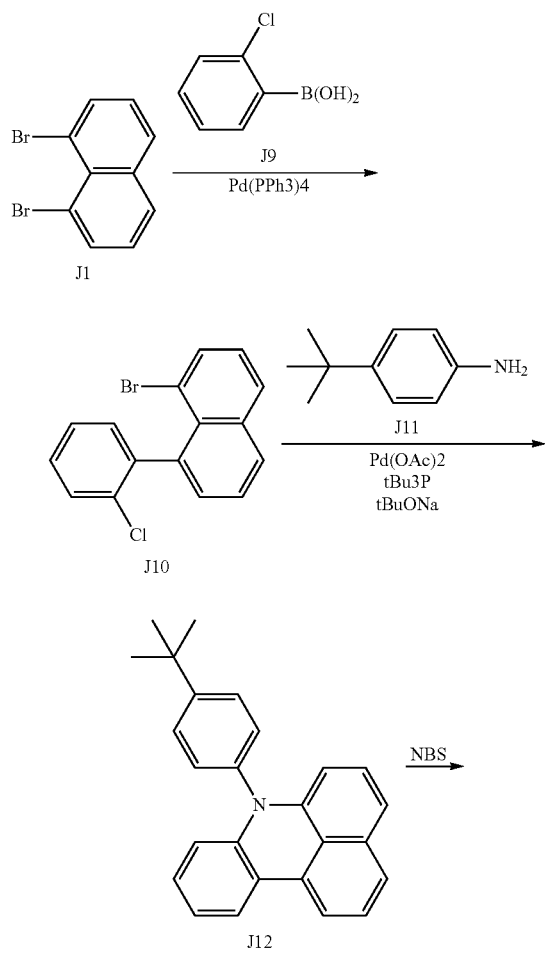

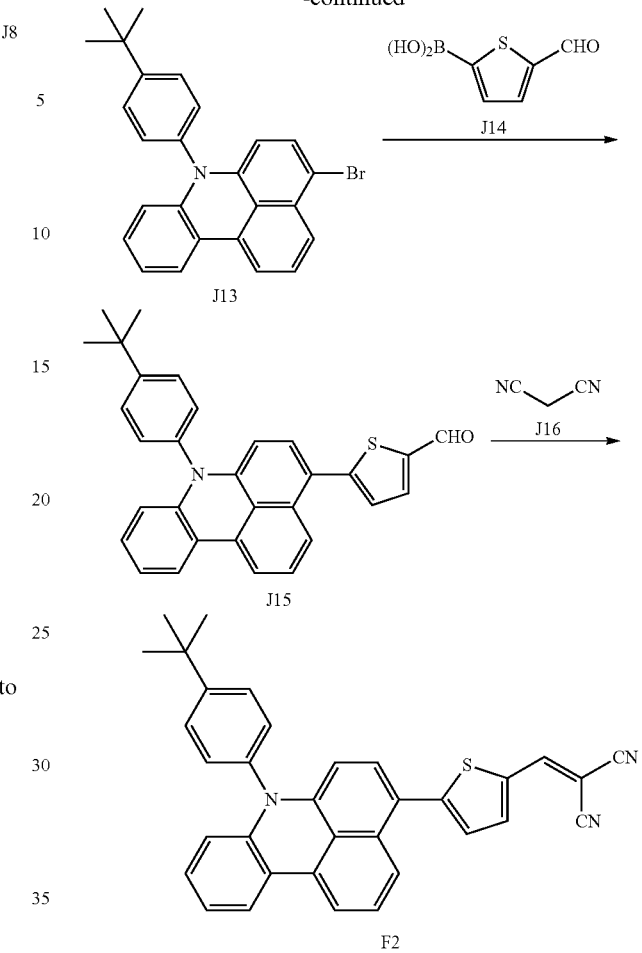

(1) Synthesis of Compound J10

The following regents and solvents were added into a 300 mL recovery flask:
Compound J1: 2.00 g (4.10 mmol)
Compound J9: 1.83 g (10.3 mmol)
Tetrakis(triphenylphosphine)palladium (0): 95 mg (0.08 mmol)
Toluene: 40 mL
Ethanol: 20 mL
2M cesium carbonate aqueous solution: 40 mL Next, the resulting reaction solution was heated to reflux for 7 hours with stirring in a nitrogen atmosphere. After the reaction, the reaction product was extracted with chloroform. The organic phase obtained by extraction was dehydrated with sodium sulfate and was subsequently concentrated under reduced pressure to yield a crude product. Subsequently, the crude product was purified by silica gel chromatography (eluent: chloroform/heptane=1/10) to yield 1.55 g of Compound J10 (yield: 75%).

(2) Synthesis of Compound J12

The following regents and solvent were added into a 300 mL flask:
Compound J10: 2.00 g (6.98 mmol)
Compound J11: 1.38 g (6.98 mmol)
Palladium acetate: 0.10 g (0.36 mmol)
tert-Butylphosphine: 0.20 g (0.70 mmol)
Sodium tert-butoxide: 2.01 g (21 mmol)
Dehydrated toluene: 70 mL Next, the resulting reaction solution was heated to reflux for 7 hours with stirring in a nitrogen atmosphere. After the reaction, the solution was passed through a membrane filter to yield a filtrate. Then, the filtrate was washed with water, dehydrated with sodium sulfate, and concentrated under reduced pressure to yield a crude product. Subsequently, the crude product was purified by silica gel chromatography (eluent: toluene/heptane=1/4) to yield 1.50 g of Compound J12 (yield: 67%).

(3) Synthesis of Compound J13

The following regent and solvent were added into a 100 mL flask:
Compound J10: 1.50 g (4.67 mmol)
Dehydrated DMF: 60 mL Subsequently, 0.83 g (4.67 mmol) of NBS was added to the resulting reaction solution with ice cooling and stirring in a nitrogen atmosphere. Then, the mixture was stirred for 1 hour at room temperature. After the reaction, the reaction solution was poured into 240 mL of water, followed by extraction with ethyl acetate. The organic phase thus obtained was dehydrated with sodium sulfate and was subsequently concentrated under reduced pressure to yield a crude product. Subsequently, the crude product was purified by silica gel chromatography (eluent: toluene/heptane=1/10) to yield 0.93 g of Compound J13 (yield: 50%).

(4) Synthesis of Compound J15

The following regents and solvents were added into a 300 mL recovery flask:
Compound J13: 2.00 g (4.10 mmol)
Compound J14: 1.83 g (10.3 mmol)
Tetrakis(triphenylphosphine)palladium (0): 95 mg (0.08 mmol)
Toluene: 40 mL
Ethanol: 20 mL
2M cesium carbonate aqueous solution: 40 mL Next, the resulting reaction solution was heated to reflux for 7 hours with stirring in a nitrogen atmosphere. After the reaction, the reaction product was extracted with chloroform. The organic phase obtained by extraction was dehydrated with sodium sulfate and was subsequently concentrated under reduced pressure to yield a crude product. Subsequently, the crude product was purified by silica gel chromatography (eluent: chloroform/heptane=1/10) to yield 1.55 g of Compound J15 (yield: 75%).

(5) Synthesis of Compound F2

The following regents and solvents were added into a 100 mL flask:
Compound J15: 0.27 g (0.77 mmol)
Compound J16: 0.17 g (1.16 mmol)
Dichloromethane: 20 mL
Triethylamine: several drops Next, the reaction solution was stirred at room temperature for 7 hours in a nitrogen atmosphere. After the reaction, the resulting liquid was passed through a membrane filter to yield a crude product. Subsequently, the crude product was purified by silica gel chromatography (eluent: toluene/heptane=1/4) to yield 0.25 g of Compound F2 (yield: 70%).

The resulting compound was identified by mass spectrometry as in Example 1.

Measured value: m/z=563.82, Calculation value: $C_{38}H_{33}N_3S$=563.75

Examples 10 to 13

Exemplified Compounds were synthesized and purified in the same manner as in Example 9, except that: Organic Compound J9 was replaced with a boric acid compound shown in the following Table 3; Organic Compound J11 was replaced with an amine compound shown in Table 3; and Organic Compound J14 was replaced with a boric acid compound having a formyl group shown in Table 3. The resulting compound was identified by mass spectrometry as in Example 1. The results are shown in Table 3.

TABLE 3

| | Compound J9 | Compound J11 | Compound J14 | Exemplified Compound | Mass analysis results |
|---|---|---|---|---|---|
| Example 10 | (2-chlorophenyl)boronic acid | 9,9-dimethyl-9H-fluoren-2-amine | 5-formylthiophen-2-yl boronic acid | F9 | Measurement (m/z): 567.25 Calculation value $C_{39}H_{25}N_3S$: 567.70 |
| Example 11 | (3-chloronaphthalen-2-yl)boronic acid | 3,5-di-tert-butylaniline | 2-formylthiazol-5-yl boronic acid | F3 | Measurement (m/z): 614.51 Calculation value $C_{41}H_{34}N_4S$: 614.80 |
| Example 12 | (4-chloropyridin-3-yl)boronic acid | benzo[b]thiophen-2-amine | 4-formyl-1,3,4-oxadiazol-2-yl boronic acid | D10 | Measurement (m/z): 494.41 Calculation value $C_{29}H_{14}N_6OS$: 494.53 |

TABLE 3-continued

| | Compound J9 | Compound J11 | Compound J14 | Exemplified Compound | Mass analysis results |
|---|---|---|---|---|---|
| Example 13 | 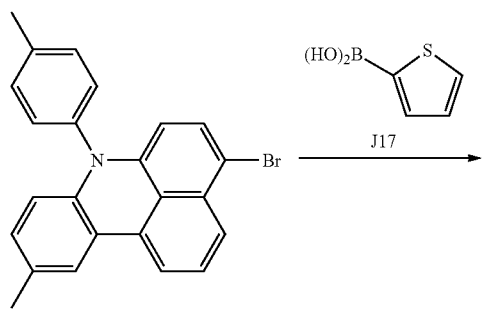 | | | F10 | Measurement (m/z): 563.82<br>Calculation value $C_{36}H_{25}N_3S_2$: 563.73 |

Example 14: Synthesis of Exemplified Compound E5

Exemplified Compound E5 was synthesized and purified in the same manner as in Example 1, except that Compound J5 was replaced with Compound J15 in the step of (4). The resulting compound was identified by mass spectrometry as in Example 1.

Measured value: m/z=587.26, Calculation value: $C_{40}H_{29}NO_2S$=587.73

Example 15: Synthesis of Exemplified Compound F6

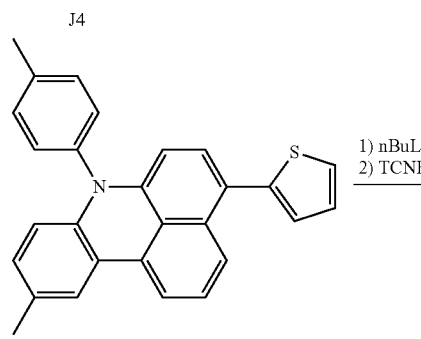

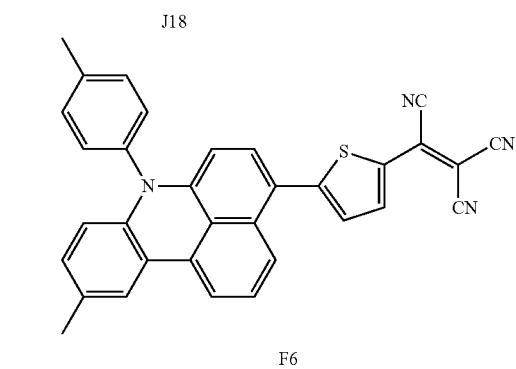

(1) Synthesis of Compound J18

The following regents and solvents were added into a 300 mL recovery flask:
Compound J4: 2.00 g (4.10 mmol)
Compound J17: 1.83 g (10.3 mmol)
Tetrakis(triphenylphosphine)palladium (0): 95 mg (0.08 mmol)
Toluene: 40 mL
Ethanol: 20 mL
2M cesium carbonate aqueous solution: 40 mL Next, the resulting reaction solution was heated to reflux for 7 hours with stirring in a nitrogen atmosphere. After the reaction, the reaction product was extracted with chloroform. The organic phase obtained by extraction was dehydrated with sodium sulfate and was subsequently concentrated under reduced pressure to yield a crude product. Subsequently, the crude product was purified by silica gel chromatography (eluent: chloroform/heptane=1/10) to yield 1.55 g of Compound J18 (yield: 75%).

(2) Synthesis of Compound F6

The following regent and solvent were added into a 100 mL flask:
Compound J18: 0.90 g (2.33 mmol)
Dehydrated THF: 20 mL Into the resulting reaction solution was dropped 1.50 mL (3.50 mmol) of 1.6 M solution of n-butyllithium in n-hexane with stirring at −80° C. in a nitrogen atmosphere, followed by stirring for 1 hour. Subsequently, 0.35 mL (4.66 mmol) of dehydrated DMF was dropped into the reaction solution, followed by heating slowly to room temperature. After the reaction, the reaction solution was poured into 100 mL of 1 N HCl aqueous solution, followed by extraction with ethyl acetate. The organic phase thus obtained was dehydrated with sodium sulfate and was subsequently concentrated under reduced pressure to yield a crude product. Subsequently, the crude product was purified by silica gel chromatography (eluent: toluene/heptane=1/1) to yield 0.33 g of Compound F6 (yield: 41%).

The resulting compound was identified by mass spectrometry as in Example 1.

Measured value: m/z=504.86, Calculation value: $C_{33}H_{20}N_4S$=504.66

Example 16

In Example 16, a photoelectric conversion element was produced which includes a hole collecting electrode, an electron blocking electrode, a photoelectric conversion layer, a hole blocking layer, and an electron collecting layer in this order on a substrate.

First, IZO was deposited on a Si substrate, and the IZO film was subjected to a patterning to form an IZO electrode (hole collecting electrode). The thickness of the resulting IZO electrode was 100 nm. The substrate thus provided with the hole collecting electrode thereon was used as an electrode-attached substrate in the following step.

Organic compound layers and an electrode layer, shown in the following Table 4, were successively formed on the electrode-attached substrate. The photoelectric conversion layer was formed to a thickness shown in Table 4 by codeposition of compounds in the ratio shown in the Table. At this time, the opposing electrode (electron collecting electrode) was formed to have an area of 3 mm².

TABLE 4

| | Constituent | Thickness (nm) |
|---|---|---|
| Electron blocking layer | EB1 | 100 |
| Photoelectric conversion layer | Exemplified Compound A2:Fullerene C60 = 25:75 (mass ratio) | 400 |
| Hole blocking layer | Fullerene C60 | 50 |
| Electron collecting electrode | Indium zinc oxide | 30 |

Examples 17 to 25, Comparative Example 1

Organic photoelectric conversion elements were prepared in the same manner as in Example 16, except that the electron blocking layer, the photoelectric conversion layer, and the hole blocking layer were replaced with those shown in the following Table 5.

Evaluation of Organic Photoelectric Conversion Elements

A voltage of 5 V was applied to each of the resulting elements, and the external quantum efficiency at that time was determined. The external quantum efficiency was determined by measuring the photocurrent density when the element was irradiated with each of the monochromatic light beams of 50 µW/cm² in intensity each having a wavelength of 450 nm, 500 nm, or 600 nm in a state where a voltage of 10 V was applied between the hole collecting electrode and the electron collecting electrode of the element. In this instance, the photocurrent density was calculated by subtracting the dark current density during light blocking from the current density during light irradiation. For the monochromatic light beams used for measuring photocurrent density, white light emitted from a xenon lamp XB-50101AA-A, manufactured by Ushio Inc., was monochromatized with a monochromator MC-10N manufactured by Ritu Oyo Kougaku. For applying a voltage to the element and measuring current, a source meter R6243 manufactured by Advantest was used. For measuring the internal light absorptance and external quantum efficiency of the element, light was introduced into the element from the upper electrode (electron collecting electrode) side in the direction perpendicular to the element. The results are shown in Table 6.

In addition, each organic photoelectric conversion element was examined for variation between the external quantum efficiencies before and after annealing. The stability of each element after annealing was evaluated according to the following criteria: when the external quantum efficiency after annealing at the maximum wavelength of an element was 0.9 or more relative to that before annealing, the element was graded as A; when it was in the range of 0.7 to less than 0.9, the element was graded as B; and when it was less than 0.7, the element was graded as C. The

TABLE 5

| | Electron blocking layer | Photoelectric conversion layer | Hole blocking layer |
|---|---|---|---|
| Example 17 | EB1 | Exemplified Compound B1:Fullerene C60 = 25:75 (weight ratio) | Fullerene C60 |
| Example 18 | EB1 | Exemplified Compound D1:Fullerene C60 = 20:80 (weight ratio) | Fullerene C60 |
| Example 19 | EB2 | Exemplified Compound C1:Fullerene C60 = 30:70 (weight ratio) | HB1 |
| Example 20 | EB2 | Exemplified Compound G3:Fullerene C60 = 25:75 (weight ratio) | HB2 |
| Example 21 | EB2 | Exemplified Compound H4:Fullerene C60 = 25:75 (weight ratio) | Fullerene C60 |
| Example 22 | EB2 | Exemplified Compound E5:Fullerene C60 = 25:75 (weight ratio) | [60]PCBM |
| Example 23 | Exemplified Compound A2:EB1 = 10:90 (weight ratio) | Exemplified Compound F1:Fullerene C60 = 25:75 (weight ratio) | Fullerene C60 |
| Example 24 | EB3 | Exemplified Compound F6:Fullerene C60 = 30:70 (weight ratio) | Exemplified Compound A1:Fullerene C60 = 10:90 (weight ratio) |
| Example 25 | EB3 | Exemplified Compound A1:Exemplified Compound B1:Fullerene C60 = 10:20:70 (weight ratio) | Fullerene C60 |
| Comparative Example 1 | EB1 | Comparative Compound 1:Fullerene C60 = 25:75 (weight ratio) | Fullerene C60 | annealing was performed by allowing the element on a hot plate of 150° C. in the air for 30 minutes.

TABLE 6

|  | External quantum efficiency | | | Relative external quantum efficiency* |
| --- | --- | --- | --- | --- |
|  | @450 nm | @500 nm | @600 nm | after annealing |
| Example 16 | Excellent | Excellent | Excellent | A |
| Example 17 | Excellent | Good | Good | B |
| Example 18 | Excellent | Excellent | Good | B |
| Example 19 | Excellent | Excellent | Good | B |
| Example 20 | Excellent | Good | Good | A |
| Example 21 | Good | Good | Good | A |
| Example 22 | Good | Excellent | Excellent | A |
| Example 23 | Good | Excellent | Excellent | A |
| Example 24 | Good | Good | Excellent | A |
| Example 25 | Excellent | Excellent | Excellent | A |
| Comparative Example 1 | Excellent | Good | Bad | C |

Excellent: External quantum efficiency was 50% or more.
Good: External quantum efficiency was in the range of 30% to less than 50%.
Bad: External quantum efficiency was less than 30%.
A: Relative external quantum efficiency after annealing was 0.9 or more.
B: Relative external quantum efficiency after annealing was in the range of 0.8 to less than 0.9.
C: Relative external quantum efficiency after annealing was less than 0.8.
(*Relative to the external quantum efficiency before annealing)

Table 6 shows that the organic photoelectric conversion elements using any of the compounds according to the present disclosure exhibited a high external quantum efficiency for light in each of a blue region (around a wavelength of 450 nm), a green region (around a wavelength of 500 nm), and a red region (around a wavelength of 600 nm), suggesting that these photoelectric conversion elements can efficiently convert light energy over the entire region of visible wavelengths into electrical energy. On the other hand, the organic photoelectric conversion element of the Comparative Example exhibited a low photoelectric conversion efficiency for light having a wavelength of 600 nm.

The reason of these results is that the compounds in the organic photoelectric conversion elements according to the present disclosure have a high absorption coefficient in a long wavelength region.

In addition, the organic photoelectric conversion elements of the Examples kept the photoelectric conversion performance stable. This is because the compounds in the organic photoelectric conversion elements according to the present disclosure have a high glass transition temperature.

As just described for the Examples, the organic compound represented by general formula [1] enables the photoelectric conversion layer to efficiently convert energy of light over the entire region of visible light into electrical energy when added into the photoelectric conversion layer, and also makes the organic photoelectric conversion element thermally stable.

The present disclosure provides a thermally stable organic compound having a high absorption coefficient in a long wavelength region. Furthermore, use of the organic compound provides a thermally stable organic photoelectric conversion element and imaging device that can exhibit satisfactory photoelectric conversion performance.

While the present disclosure has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2017-200399 filed Oct. 16, 2017, which is hereby incorporated by reference herein in its entirety.

What is claimed is:

1. An organic compound represented by the following formula [1]:

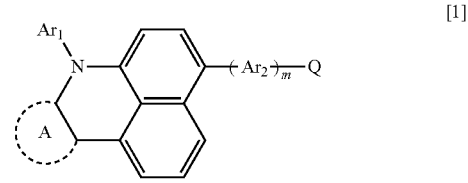

[1]

wherein in formula [1], $Ar_1$ and $Ar_2$ each represent a group independently selected from the group consisting of aryl groups having a carbon number of 6 to 18 and heteroaryl groups having a carbon number of 3 to 15, and A represents a cyclic structure selected from the group consisting of a benzene ring, a naphthalene ring, a phenanthrene ring, a fluorene ring, a pyridine ring, a thiophene ring, a benzothiophene ring, a furan ring, and a benzofuran ring, wherein $Ar_1$, $Ar_2$, and A each may have a substituent selected from the group consisting of halogen atoms, a cyano group, alkyl groups having a carbon number of 1 to 6, alkoxy groups having a carbon number of 1to 6, a trifluoromethyl group, a phenyl group, a tolyl group, a xylyl group, and a mesityl group;

m represents an integer of 0 to 2, and when m is 2, the two $Ar_2$'s may be the same as or different from each other; and Q represents an electron-withdrawing substituent represented by one of the following formulas [1-1] and [1-2]:

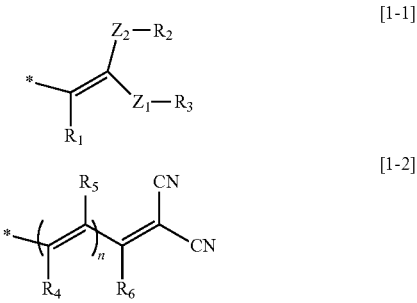

wherein in formulas [1-1] and [1-2],

* represents a bonding site;

$R_1$ to $R_6$ each represent a chemical species independently selected from the group consisting of a hydrogen atom, a cyano group, an amino group, alkylamino groups having a carbon number of 1 to 4, amide groups having a carbon number of 1 to 4, alkenyl groups having a carbon number of 2 to 4, alkynyl groups having a carbon number of 2 to 4, a methoxy group, an ethoxy group, a methyl group, an ethyl group, an isopropyl group, a tert-butyl group, a phenyl group, and a pyridyl group, wherein the chemical species $R_1$ to $R_6$ each may have a substituent selected from the group consisting of a chlorine atom, a fluorine atom, a cyano group, a methyl group, a tert-butyl group, a methoxy group, an ethoxy group, a phenyl group, a tolyl group, a xylyl group, and a mesityl group, R₂ and R₃ may be bound to each other to form a ring, and R₄ and R₆ may be bound to each other to form a ring;

n represents an integer of 0 to 2, and when n is 2, the two R₄'s may be the same as or different from each other and the two R₅'s may be the same as or different from each other; and Z₁ and Z₂ each represent a structure represented by one of the following formulas [2-1] to [2-3]:

[2-1]
[2-2]
[2-3]

wherein in formulas [2-1] to [2-3], * represents a bonding site.

2. The organic compound according to claim 1, the organic compound being represented by the following formula [4]:

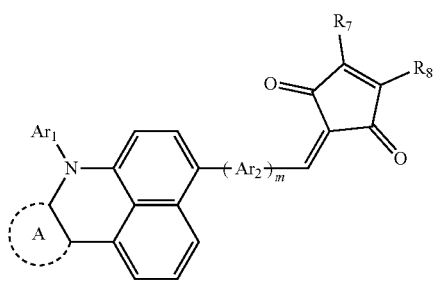

[4]

wherein in formula [4],

R₇ and R₈ each represents a chemical species independently selected from the group consisting of a hydrogen atom, a fluorine atom, a chlorine atom, a cyano group, a methyl group, a tert-butyl group, a methoxy group, an ethoxy group, a trifluoromethyl group, a phenyl group, a tolyl group, a xylyl group, a pyridyl group, and a thienyl group, wherein R₇ and R₈ may have a substituent selected from the group consisting of a fluorine atom, a cyano group, a methyl group, a tert-butyl group, a methoxy group, a phenyl group, and a thienyl group and may be bound to each other to form a ring.

3. The organic compound according to claim 2, wherein the ring formed by binding R₇ and R₈ to each other is selected from the group consisting of a benzene ring, a naphthalene ring, a pyridine ring, a pyrimidine ring, a pyrazine ring, a pyridazine ring, a quinoline ring, an isoquinoline ring, a quinoxaline ring, a thiophene ring, a benzothiophene ring, a furan ring, and a benzofuran ring.

4. The organic compound according to claim 1, the organic compound being represented by the following formula [5]:

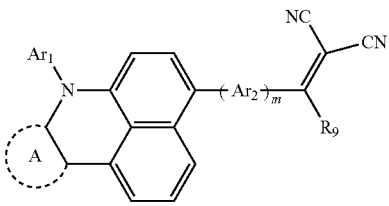

[5]

wherein in formula [5], R₉ represents a chemical species selected from the group consisting of a hydrogen atom, a fluorine atom, a chlorine atom, a cyano group, a methyl group, a tert-butyl group, a methoxy group, an ethoxy group, a trifluoromethyl group, a phenyl group, a tolyl group, a xylyl group, a pyridyl group, and a thienyl group and may have a substituent selected from the group consisting of a fluorine atom, a cyano group, a methyl group, a tert-butyl group, a methoxy group, and a phenyl group.

5. The organic compound according to claim 1, wherein Ar₂ represents a member selected from the group consisting of a thienyl group, a thienothienyl group, and a furanyl group.

6. The organic compound according to claim 1, wherein m represents 0 or 1.

7. The organic compound according to claim 1, wherein A represents a benzene ring or a naphthalene ring.

8. A photoelectric conversion element comprising:
an electron collecting electrode;
a hole collecting electrode; and
an organic compound layer between the electron collecting electrode and the hole collecting electrode, the organic compound layer containing the organic compound as set forth in claim 1.

9. The photoelectric conversion element according to claim 8, wherein the organic compound layer includes a photoelectric conversion layer containing an n-type organic semiconductor.

10. The photoelectric conversion element according to claim 9, wherein the n-type organic semiconductor is a fullerene or a fullerene derivative.

11. An imaging device comprising:
the photoelectric conversion element as set forth in claim 8;
a readout circuit connected to the photoelectric conversion element; and
a signal processing circuit connected to the readout circuit.

12. An imaging unit:
an imaging optical system; and
the imaging device as set forth in claim 11, the imaging device being operable to receive light that has passed through the imaging optical system.

13. An imaging unit comprising:
the imaging device as set forth in claim 11; and
an enclosure housing the imaging device, the enclosure including a joint section capable of being connected to an imaging optical system.

14. The imaging unit according to claim 12, further comprising a signal receiver operable to receive a signal from the outside thereof, the signal being used for controlling at least one of an imaging range thereof, an imaging start point thereof, and an imaging end point thereof.

15. The imaging unit according to claim 12, further comprising a transmitter operable to transmit an obtained image to the outside thereof.

16. An organic compound represented by the following formula [1]:

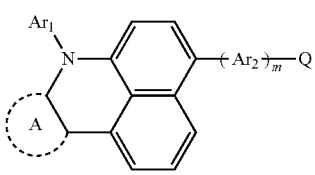

[1]

wherein in formula [1],

Ar$_1$ and Ar$_2$ each represent a group independently selected from the group consisting of aryl groups and heteroaryl groups, and A represents a cyclic structure, wherein Ar$_1$, Ar$_2$, and A each may have a substituent;

m represents an integer of 0 to 2, and when m is 2, the two Ar$_2$'s may be the same as or different from each other; and Q represents an electron-withdrawing substituent represented by one of the following formulas [1-1] and [1-2]:

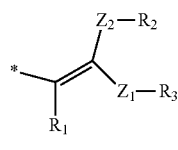

[1-1]

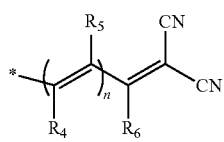

[1-2]

wherein in formulas [1-1] and [1-2],

* represents a bonding site;

R$_1$ to R$_6$ each represent a chemical species independently selected from the group consisting of a hydrogen atom, a cyano group, an amino group, alkylamino groups, amide groups, alkenyl groups, alkynyl groups, an alkoxy groups, an alkyl groups, an aryl groups, and a heterocyclic groups, wherein the chemical species R$_1$ to R$_6$ each may have a substituent, R$_2$ and R$_3$ may be bound to each other to form a ring, and R$_4$ and R$_6$ may be bound to each other to form a ring;

n represents an integer of 0 to 2, and when n is 2, the two R$_4$'s may be the same as or different from each other and the two R$_5$'s may be the same as or different from each other; and Z$_1$ and Z$_2$ each represent a structure represented by one of the following formulas [2-1] to [2-3]:

[2-1]

[2-2]

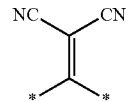

[2-3]

wherein in formulas [2-1] to [2-3], * represents a bonding site.

* * * * *